United States Patent [19]
Harrison et al.

[11] Patent Number: 5,606,063
[45] Date of Patent: Feb. 25, 1997

[54] NMDA ANTAGONISTS

[75] Inventors: Boyd L. Harrison; Bruce M. Baron, both of Cincinnati; David M. Stemerick, Fairfield; Ian A. McDonald, Loveland, all of Ohio

[73] Assignee: Merrell Pharmaceuticals Inc., Cincinnati, Ohio

[21] Appl. No.: 462,406

[22] Filed: Jun. 5, 1995

Related U.S. Application Data

[63] Continuation of Ser. No. 305,614, Sep. 14, 1994, abandoned, which is a continuation of Ser. No. 156,661, Nov. 22, 1993, abandoned, which is a continuation of Ser. No. 832,528, Feb. 7, 1992, abandoned, which is a continuation-in-part of Ser. No. 700,004, May 14, 1991, abandoned, which is a continuation-in-part of Ser. No. 661,780, Feb. 27, 1991, abandoned.

[51] Int. Cl.$^6$ ................................................ C07D 215/06
[52] U.S. Cl. ................................................ 546/159; 546/162
[58] Field of Search ................................ 546/159, 162; 514/313

[56] References Cited

U.S. PATENT DOCUMENTS 5,026,700  6/1991  Harrison et al. .................... 514/233.8

FOREIGN PATENT DOCUMENTS 0303387  2/1989  European Pat. Off. .
0386839  3/1990  European Pat. Off. .
0398283  11/1990  European Pat. Off. .

OTHER PUBLICATIONS

Wright, Synthens, 1984, Dec. pp. 1058–1061.
Journal of Medicinal Chemistry, vol. 33, No. 12, 1990, B. L. Harrison et al.: "4-[(Carboxymethyl)oxyl]-and 4-[(carboxymethyl)amino]-5,7-dichloroquinoline-2-c arboxylic acid: New antagonists of the strychnine-insensitive glycine binding site on the N-methyl-D-aspartate receptor complex".

*Primary Examiner*—Brian M. Burn
*Attorney, Agent, or Firm*—Michael J. Sayles

[57] ABSTRACT

The present invention is directed to a new class of 4-sulfanimide-quinoline derivatives and to their use as NMDA antagonists.

82 Claims, No Drawings

NMDA ANTAGONISTS

This is a continuation of application Ser. No. 08/305,614 filed Sep. 14, 1994, now abandoned; which is a continuation of application Ser. No. 08/156,661, filed Nov. 22, 1993, now abandoned; which is a continuation of application Ser. No. 07/832,528, filed Feb. 7, 1992, now abandoned, which is a continuation-in-part of application Ser. No. 07/700,004, filed May 14, 1991, now abandoned; which is a continuation-in-part of application Ser. No. 07/661,780, filed Feb. 27, 1991 now abandoned which is herein incorporated by reference.

The present invention is directed to a new class of excitatory amino acid antagonists. Another aspect of the invention is directed to methods for the treatment of epilepsy, neurodegenerative diseases such as Huntington's disease, and for preventing ischemic/hypoxic damage to nervous tissues contained within the central nervous system. A further aspect of the invention is directed towards pharmaceutical formulations containing these excitatory amino acid antagonists.

In accordance with the present invention, a new class of excitatory amino acid antagonists which act at the NMDA receptor complex has been discovered. These compounds can be represented by the following formula:

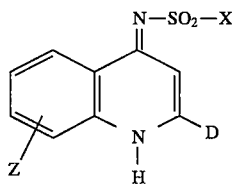

Formula I in which D is represented $C(O)OR_1$ or $C(O)NR_1R_2$; $R_1$ and $R_2$, are each independently represented by hydrogen or $C_1$–$C_6$ alkyl; Z is represented by a substituent selected from the group consisting of hydrogen, OH, halogen, CN, $NO_2$, $C_1$–$C_6$ alkyl, $C_1$–$C_6$ alkoxy, $OCF_3$ and $CF_3$; X is represented by one of the following substituents:

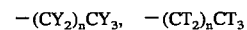

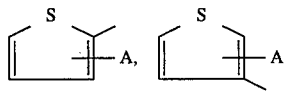

in which Y is represented by Cl; T is represented by F; n is represented by an integer from 0–3; A is represented by a substituent selected from the group consisting of hydrogen, OH, halogen, CN, $NO_2$, $C_1$–$C_6$ alkyl, $C_1$–$C_6$ alkoxy, $OCF_3$ or $CF_3$; B is represented by one substituent selected from the group consisting of hydrogen, $C(O)OR_1$, $C(O)NR_1R_2$, $NH_2$, $NR_1R_2$, $NHC(O)R_3$, $NHC(O)OR_3$, $NHC(O)NHR_3$, $NH-SO_2-CF_3$, $NH-SO_2-C_6H_5$; in which $R_1$ and $R_2$ are as defined above; $R_3$ is $C_1$–$C_6$ alkyl; the pharmaceutically acceptable salts thereof and the tautomers thereof, with the proviso: 1) that when D is $C(O)OCH_3$ and X is phenyl in which A is para-methyl and B is hydrogen, then Z is not hydrogen, or a 5,7-dichloro substituent; 2) that when D is $C(O)OC_2H_5$ and X is phenyl in which A is para-methyl and B is hydrogen, then Z is not 6-methoxy, 7-methoxy or 5,8-dimethoxy and 3) that when B is not hydrogen, the total of A plus B may be up to 3 substituents.

The two compounds encompassed by the first proviso above (ie. methyl 4-(p-toluenesulfonylimino)-1,4-dihydroquinoline-2-carboxylate and methyl 5,7-dichloro-4-(p-toluenesulfonylimino)-1,4-dihydroquinoline-2-carboxylate (named 5,7-dichloro-4-[(4-methyl)benzenesulfonimide]-1,4-dihydroquinoline-2-carboxylic acid, methyl ester in the present application) are active as excitatory amino acid antagonists. They have been described as intermediates in European Application 0 398 283. Those compounds encompassed by the second proviso where disclosed by Wright, in Synthesis, 1984, 1058. They are also active as excitatory amino acid antagonists. The compounds encompassed by these two provisos should be considered within the scope of any method, use, or formulation claim.

DETAILED DESCRIPTION OF THE INVENTION

As used in this application:

a) the term "halogen" refers to a fluorine, chlorine, or bromine atom;

b) the terms "lower alkyl group and $C_{1-6}$ alkyl" refer to a branched or straight chained alkyl group containing from 1–6 carbon atoms, such as methyl, ethyl, n-propyl, isopropyl, n-butyl, isobutyl, n-pentyl, n-hexyl, etc;

c) the terms "lower alkoxy group and $C_{1-6}$ alkoxy" refer to a straight or branched alkoxy group containing from 1–6 carbon atoms, such as methoxy, ethoxy, n-propoxy, isopropoxy, n-butoxy, isobutoxy, n-pentoxy, n-hexoxy, etc;

d) the term "phenyl derivative" refers to:

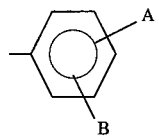

e) the term "2-thiophene derivative" refers to:

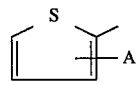

f) the term "3-thiophene derivative" refers to:

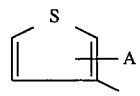

g) the term "pharmaceutically acceptable salts thereof" refers to either an acid addition salt or a basic addition salt;

h) the term "$C_6H_5$" refers to an unsubstituted phenyl ring.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

As is readily apparent to those skilled in the art, the compounds of Formula I will exist as tautomers. Any reference to the compounds of Formula I or an intermediate thereof should be construed as referring to either tautomer. These tautomers may be depicted as:

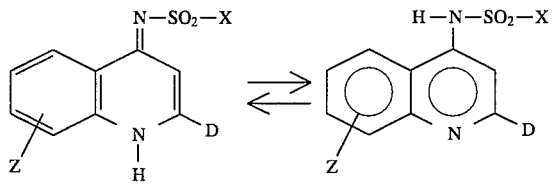

As is indicated by the Z substituent, the quinoline nucleus may be optionally substituted. The quinoline nucleus is always substituted at the 2-position with either a carboxylic acid or a derivative thereof and at the 4-position with the sulfonimide depicted. Positions 3, 5, 6, 7, or 8 may be optionally substituted with the substituents encompassed by Z. Z may represent up to 3 non-hydrogen substituents. These non-hydrogen substituents may be the same or different.

X may be represented by a phenyl ring. When X is a phenyl ring, it may be optionally substituted as is indicated by the A and B substituents. A may be represented by up to 3 non-hydrogen substituents when B is hydrogen. These substituents may be the same or different. They may be located at any of the ortho, meta, or para positions. B may only be represented by one non-hydrogen substituent. It may be located at any of the ortho, meta, or para positions. When B is not hydrogen, then up to 2 A substituents may also be present on the phenyl ring.

X may also be represented by a thiophene ring. The thiophene ring may also be optionally substituted as indicated by the A substituent. A may represent up to 2 non-hydrogen substituents which may be the same or different. These non-hydrogen substituents may be bonded to positions 2, 4, 5 of a 3-thiophene ring or 3, 4, 5 of a 2-thiophene ring.

It is currently preferred for A to be a phenyl substituent and more preferably 4-aminophenyl and for Z to be a 5,7-dihalogen and more preferably 5,7-dichloro; 5,7-dibromo, 5-bromo-7-chloro and 5-bromo-7-fluoro.

Examples of compounds encompassed by the present invention include:

5,7-Dichloro-4-[4-(trifluoromethyl)benzenesulfonimide]-1,4-dihydroquinoline-2-carboxylic acid, methyl ester;
5,7-Dichloro-4-[4-(trifluoromethyl)benzenesulfonimide]-1,4-dihydroquinoline-2-carboxylic acid;
5,7-Dichloro-4-[4-(fluoro)benzenesulfonimide]-1,4-dihydroquinoline-2-carboxylic acid, methyl ester;
5,7-Dichloro-4-[4-(fluoro)benzenesulfonimide]-1,4-dihydroquinoline-2-carboxylic acid;
5,7-Dichloro-4-[(2-thiophene)sulfonimide]-1,4-dihydroquinoline-2-carboxylic acid, methyl ester;
5,7-Dichloro-4-[(2-thiophene)sulfonimide]-1,4-dihydroquinoline-2-carboxylic acid;
5,7-Dichloro-4-[4-(methoxy)benzenesulfonimide]-1,4-dihydroquinoline-2-carboxylic acid, methyl ester;
5,7-Dichloro-4-[4-(methoxy)benzenesulfonimide]-1,4-dihydroquinoline-2-carboxylic acid;
5,7-Dichloro-4-[benzenesulfonimide]-1,4-dihydroquinoline-2-carboxylic acid, methyl ester;
5,7-Dichloro-4-[benzenesulfonimide]-1,4-dihydroquinoline-2-carboxylic acid;
5,7-Dichloro-4-[(4-methyl)benzenesulfonimide]-1,4-dihydroquinoline-2-carboxylic acid, methyl ester;
5,7-Dichloro-4-[(4-methyl)benzenesulfonimide]-1,4-dihydroquinoline-2-carboxylic acid;
5,7-Dichloro-4-[(4-chloro)benzenesulfonimide]-1,4-dihydroquinoline-2-carboxylic acid, methyl ester;
5,7-Dichloro-4-[(4-chloro)benzenesulfonimide]-1,4-dihydroquinoline-2-carboxylic acid;
5,7-Dichloro-4-[trifluoromethylsulfonimide]-1,4-dihydroquinoline-2-carboxylic acid, methyl ester;
5,7-Dichloro-4-[trifluoromethylsulfonimide]-1,4-dihydroquinoline-2-carboxylic acid;
5,7-Dichloro-4-[2-chlorobenzenesulfonimide]-1,4-dihydroquinoline-2-carboxylic acid, methyl ester;
5,7-Dichloro-4-[2-chlorobenzenesulfonimide]-1,4-dihydroquinoline-2-carboxylic acid;
5,7-Dichloro-4-[3-chlorobenzenesulfonimide]-1,4-dihydroquinoline-2-carboxylic acid, methyl ester;
5,7-Dichloro-4-[3-chlorobenzenesulfonimide]-1,4-dihydroquinoline-2-carboxylic acid;
5,7-Dichloro-4-[4-(methylcarbamoyl)-3-chlorobenzenesulfonimide]-1,4-dihydroquinoline-2-carboxylic acid, methyl ester;
5,7-Dichloro-4-[4-amino-3-chlorobenzenesulfonimide]-1,4-dihydroquinoline-2-carboxylic acid;
5,7-Dichloro-4-[4-(methylcarbamoyl)-2-chlorobenzenesulfonimide]-1,4-dihydroquinoline-2-carboxylic acid, methyl ester;
5,7-Dichloro-4-[4-amino-2-chlorobenzenesulfonimide]-1,4-dihydroquinoline-2-carboxylic acid.

The compounds of Formula I are excitatory amino acid antagonists. They antagonize the effects which excitatory amino acids have upon the NMDA receptor complex. They preferentially bind to the strychnine-insensitive glycine binding site associated with the NMDA receptor complex. They are useful in the treatment of a number of disease states.

The compounds exhibit anti-convulsant properties and are useful in the treatment of epilepsy. They are useful in the treatment of grand mal seizures, petit mal seizures, psychomotor seizures, autonomic seizures, etc. One method of demonstrating their anti-epileptic properties is by their ability to inhibit the seizures that are caused by the administration of quinolinic acid. This test can be conducted in the following manner.

One group containing ten mice are administered 0.01–100 μg of test compound intracerebroventricularly in a volume of 5 microliters of saline. A second control group containing an equal number of mice are administered an equal volume of saline as a control. Approximately 5 minutes later, both groups are administered 7.7 micrograms of quinolinic acid intracerebroventricularly in a volume of 5 microliters of saline. The animals are observed for 15 minutes thereafter for signs of clonic-tonic seizures. The control group will have a statistically higher rate of clonic-tonic seizures than will the test group.

Another method of demonstrating the anti-epileptic properties of these compounds is by their ability to inhibit audiogenic convulsions in DBA/2 mice. This test can be conducted in the following manner. Typically one group of from 6–8 male DBA/2J audiogenic susceptible mice are administered from about 0.01 µg to about 100 µg of the test compound. The test compound is administered intracerebrally into the lateral ventricle of the brain. A second group of mice are administered an equal volume of saline control by the same route. Five minutes later the mice are placed individually in glass jars and are exposed to a sound stimulus of 110 decibels for 30 seconds. Each mouse is observed during the sound exposure for signs of seizure activity. The control group will have a statistically higher incidence of seizures than the group which receives the test compound.

The compounds of Formula I are useful for preventing or minimizing the damage which nervous tissues contained within the CNS suffer upon exposure to either ischemic, hypoxic, or hypoglycemic conditions or as the result of physical trauma. Representative examples of such conditions include strokes or cerebrovascular accidents, hyperinsulinemia, cardiac arrest, physical trauma, drownings, suffocation, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds are also useful in the treatment of neurodegenerative diseases such as Huntington's disease, Alzheimer's disease, senile dementia, glutaric acidaemia type I, Parkinson's disease, multi-infarct dementia, Lathyrism, amyotrophic lateral sclerosis, olivoponto cerebellar atrophy, motoneurone disease and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease, or a lack of oxygen or sugar. As used in this application, the term "treat" refers to the ability of the compounds to prevent further damage or delay the rate at which any further damage occurs. The compounds are also useful for treating musculoskeletal disorders of neurenal origin such as spasticity or myoclonus.

The compounds exhibit an anxiolytic effect and are thus useful in the treatment of anxiety. These anxiolytic properties can be demonstrated by their ability to block distress vocalizations in rat pups. This test is based upon the phenomenon that when a rat pup is removed from its litter, it will emit an ultrasonic vocalization. It was discovered that anxiolytic agents block these vocalizations. The testing methods have been described by Gardner, C. R., Distress vocalization in rat pups: a simple screening method for anxiolytic drugs. *J. Pharmacol. Methods,* 14:181–187 (1985) and Insel et al. Rat pup ultrasonic isolation calls: Possible mediation by the benzodiazepine receptor complex. *Pharmacol. Biochem. Behav.,* 24:1263–1267 (1986).

The compounds also exhibit an analgesic effect and are useful in controlling pain. The compounds may also be co-administered with a narcotic analgesic such as morphine, demerol, etc. When co-administered, the compounds decrease the rate at which patients develop tolerance to the pharmacological effects of these narcotics. It is also believed that this co-administration will help to prevent the patient from becoming addicted to the narcotic. The compounds are also effective in the treatment of migraine. The compounds may be utilized either prophylactically to prevent the occurrence of a migraine or during a migraine episode to terminate the migraine symptoms.

In order to exhibit these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 50 mg/kg/day for any of the diseases or conditions listed above. Repetitive daily administration may be desirable and will vary according to the conditions outlined above.

It has been discovered that probenecid will potentiate the therapeutic activity of the excitatory amino acid antagonists of the present invention. Thus the compounds will exhibit their therapeutic effects at lower doses and for longer periods in patients who are concurrently receiving probenecid. The mechanism by which probenecid potentiates their effects is not fully understood, however it is believed that probenecid decreases the rate at which the compounds are removed from the central nervous system as well as decreasing the rate of excretion by the kidneys. Probenecid increases the effective concentration of these compounds in both the CNS and in the systemic circulation.

Probenecid is known in the art. It is available commercially from Merck Sharp and Dohme under the tradename Benemid® as well as being available from numerous other sources. Probenecid is a uricosuric agent and is utilized in the treatment of gout. Probenecid is a renal tubular transport blocking agent and has been utilized to increase plasma levels of penicillin. The pharmacology of probenecid is described in detail in the 45th Edition of the Physicians Desk reference on page 1379. Probenecid is currently available commercially as tablets. The sodium salt of probenecid is readily water soluble and injectable dosage forms can be prepared from this salt using techniques well known to those skilled in the art.

The compounds of the invention may be administered concurrently with probenecid in order to treat any of the diseases or conditions described above. The quantity of probenecid that is required to potentiate the therapeutic effects of the compounds can vary widely depending upon the particular compound being administered, the patient, and the presence of other underlying disease states within the patient, etc. Typically though, the probenecid may be administered at a dosage of from 0.5–3g/day. Repetitive daily administration may be desirable and will vary according to the conditions outlined above. The probenecid will typically be administered from 2–4 times daily.

With the concurrent administration of probenecid, the dosage range for the excitatory amino antagonists may be adjusted lower by a factor of from 2–10. Alternatively, the compounds of Formula may be administered at the same dosage range in order to obtain an enhanced effect due to the higher therapeutic concentrations obtained.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically an antagonistic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered-as either a solution or a suspension. Illustrative Of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of Formula I and the probenecid can be administered as two different pharmaceutical dosage forms. Alternatively, in order to increase patient convenience, the compounds and the probenecid may be compounded into a single pharmaceutical dosage form. These pharmaceutical compositions can be manufactured utilizing techniques known in the art similar to those described above. Typically an antagonistic amount of the compound of Formula I and an effective amount of probenecid will be admixed with a pharmaceutically acceptable carrier.

As used in this application:
a) the term "patient" refers to warm blooded animals such as, for example, guinea pigs, mice, rats, cats, rabbits, dogs, monkeys, chimpanzees, and humans;
b) the term "treat" refers to the ability of the compounds to either relieve, alleviate, or slow the progression of the patient's disease or prophylactically prevent its occurrence or the manifestation of its symptoms;
c) the term "neurodegeneration" refers to a progressive death and disappearance of a population of nerve cells occurring in a manner characteristic of a particular disease state and leading to brain damage;
d) the phrase "concurrent administration" refers to administering the probenecid at an appropriate time so that it will potentiate the antagonistic effects of the compounds of Formula I. This may means simultaneous administration or administration at appropriate but different times. Establishing such a proper dosing schedule will be readily apparent to one skilled in the art.

The compounds of Formula I may also be admixed with any inert carrier and utilized in laboratory assays in order to determine the concentration of the compounds within the serum, urine, etc., of the patient as is known in the art.

Neurodegenerative diseases are typically associated with a loss of NMDA receptors. Thus, the compounds of Formula I may be utilized in diagnostic procedures to aid physicians with the diagnosis of neurodegenerative diseases. The compounds may be labeled with imaging agents known in the art such as isotopic atoms and administered to a patient in order to determine whether the patient is exhibiting a decreased number of NMDA receptors and the rate at which that loss is occurring.

The compounds of Formula I wherein X is a group represented by $-(CY_2)_nCY_3$, $-(CT_2)_nCT_3$, a phenyl derivative, a 2-thiophene derivative or a 3-thiophene derivative, A is a group represented hydrogen, halogen, OH, CN, $NO_2$, $C_1$–$C_6$ alkyl, $C_1$–$C_6$ alkoxy, $OCF_3$ or $CF_3$ and B is a group represented by hydrogen, $C(O)OR_1$ or $C(O)NR_1R_2$ and D is represented by $C(O)OR_1$ or $C(O)NR_1R_2$, wherein $R_1$ and $R_2$ are as previously defined may be prepared using techniques and procedures well known and appreciated by one of ordinary skill in the art. A general synthetic procedure for preparing these compounds is set forth in Scheme A. In Scheme A, all substituents unless otherwise indicated are as previously defined.

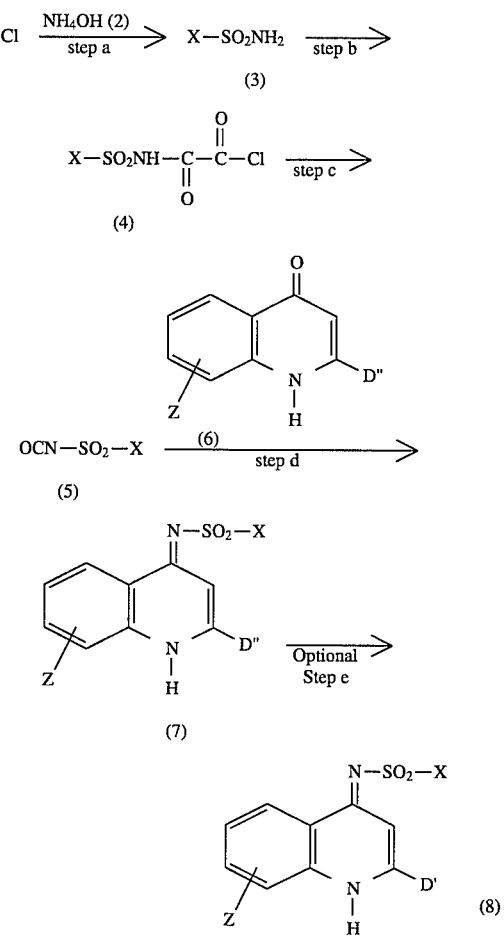

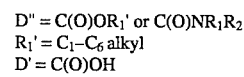

Scheme A provides a general synthetic scheme for preparing compounds of Formula I wherein X is a group represented by $-(CY_2)_nCY_3$, $-(CT_2)_nCT_3$, a phenyl derivative, a 2-thiophene derivative or a 3-thiophene derivative, A is a group represented hydrogen, halogen, OH, CN, NO$_2$, C$_1$–C$_6$ alkyl, C$_1$–C$_6$ alkoxy, OCF$_3$ or CF$_3$ and B is a group represented by hydrogen, C(O)OR$_1$ or C(O)NR$_1$R$_2$ wherein R$_1$ and R$_2$ are as previously defined and D is represented by C(O)OR$_1$ or C(O)NR$_1$R$_2$.

In step a, the appropriate sulfonyl chloride of structure (1) is amidated with ammonium hydroxide (2) to give the corresponding sulfonamide of structure (3).

For example, the appropriate sulfonyl chloride of structure (1) is contacted with a molar excess of ammonium hydroxide (2). The reactants are typically stirred together at room temperature for a period of time ranging from 10–24 hours. The sulfonamide of structure (3) is recovered from the reaction zone by evaporation of the volatiles, optional acidification with a suitable acid such as hydrochloric acid, followed by filtration.

For those sulfonyl chlorides of structure (1) wherein A is a group represented by OH or B is represented by C(O)OR$_1$, wherein R$_1$ is hydrogen, it may be necessary to protect the appropriate functionality represented by A and/or B due to the conditions of the reaction sequence. The selection and utilization of appropriate protecting groups are well known to one of ordinary skill in the art and are described in "Protective Groups in Organic Synthesis", Theodora W. Greene, Wiley (1981).

In step b, the appropriate sulfonamide of structure (3) is acylated with either oxalyl chloride, phosgene or triphosgene, oxalyl chloride being preferred, to give the corresponding N-[(1-oxo-2-oxo-2-chloro)ethyl]-sulfonamide of structure (4).

For example, the appropriate sulfonamide of structure (3) is contacted with a molar excess of oxalyl chloride, phosgene or triphosgene. The reactants are typically stirred together at a temperature range of from room temperature to reflux and for a period of time ranging from 5–24 hours. The N-[(1-oxo-2-oxo-2-chloro)ethyl]-sulfonamide of structure (4) is recovered from the reaction zone by evaporation of the volatiles.

In step c, the appropriate N-[(1-oxo-2-oxo-2-chloro)ethyl]-sulfonamide of structure (4) is converted to the corresponding sulfonyl isocyanate of structure (5).

For example, the appropriate N-[(1-oxo-2-oxo-2-chloro)ethyl]-sulfonamide of structure (4) is contacted with an appropriate anhydrous organic solvent such as o-dichlorobenzene. The reactants are typically stirred together at reflux temperature for a period of time ranging from 5–24 hours. The sulfonyl isocyanate of structure (5) is recovered from the reaction zone by fractional distillation.

Alternatively, the appropriate sulfonamide of structure (3) can be converted to the corresponding sulfonyl isocyanate of structure (5) by combining step b and step c and using a catalytic amount of a C$_1$–C$_4$ alkyl or phenyl isocyanate according to the procedure cited in *J. Org. Chem* 31 2658–61 1966.

In step d, the appropriate sulfonyl isocyanate of structure (5) is reacted with an appropriate 4-oxo-1,4-dihydroquinoline of structure (6) to give the appropriate 4-sulfonimide-1,4-dihydroquinoline of structure (7).

For example, the appropriate sulfonyl isocyanate of structure (5) is contacted with a slight molar deficiency of an appropriate 4-oxo-1,4-dihydroquinoline of structure (6). The reactants are typically contacted in a polar anhydrous organic solvent such as acetonitrile or propionitrile. The reactants are typically stirred together for a period of time ranging from 4–24 hours and at a temperature range of from room temperature to reflux. The 4-sulfonimide-1,4-dihydroquinoline of structure (7) is recovered from the reaction zone by filtration or other methods known in the art. It may be purified by recrystallization as is known in the art.

In optional step e, the ester or amide functionality of the appropriate 4-sulfonimide-1,4-dihydroquinolines of structure (7) is hydrolyzed to give the corresponding 4-sulfonimide-1,4-dihydroquinoline-2-carboxylic acids of structure (8).

For example, the appropriate 4-sulfonimide-1,4-dihydroquinoline of structure (7) wherein D is a group represented by C(O)OR$_1$ and R$_1$ is a C$_1$–C$_6$ alkyl is contacted with a suitable base, such as lithium hydroxide or sodium hydroxide. The reactants are typically stirred together for a period of time ranging from 2–24 hours and at a temperature range of from room temperature to reflux. The 4-sulfonimide-1,4-dihydroquinoline-2-carboxylic acid of structure (8) is recovered from the reaction zone by acidification followed by filtration.

In addition, any protecting groups on A and/or B may be removed under the conditions of optional step e.

Starting materials for use in the general synthetic procedures outlined in Scheme A are readily available to one of ordinary skill in the art. Certain 4-oxo-1,4-dihydroquinoline-2-carboxylic acids and amides and 4-benzyloxy-5,7-dichloroquinoline-2-carboxylic acid and acid chloride are described in European Patent Application of Leeson, Publication #0 303 387, Feb. 15, 1989 and trifluoromethylsulfonyl isocyanate is described in *J. Fluorine Chemistry* 4 83–98 1974 and certain sulfonamides of structure (3) are described in *J. Org. Chem* 31 2658–61 1966.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "μL" refers to microliters; "μg" refers to micrograms; and "μM" refers to micromolar.

EXAMPLE 1

5,7-Dichloro-4-[4-(trifluoromethyl)benzenesulfonimide]-1,4-dihydroquinoline-2-carboxylic acid, methyl ester

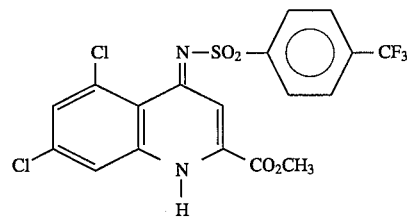

Step a: 4-(Trifluoromethyl)benzenesulfonamide

Combine 4-(trifluoromethyl)benzenesulfonyl chloride (2.5g, 0.01mol) and concentrated ammonium hydroxide (80mL). Seal and stir for 16 hours at room temperature. Heat at 90° C. to remove the ammonia and then add hydrochloric acid (1mL of a 12N solution). Cool, filter and dry to give the title compound as an off-white solid (1.61g, 72%); mp 175°–6° C.

Anal. Calcd for C$_7$H$_6$F$_3$NO$_2$S: C, 37.33; H, 2.69; N, 6.22; Found: C, 37.13; H, 2.45; N. 6.13.

Step b: N-[(1-Oxo-2-oxo-2-chloro)ethyl]-4-(trifluoromethyl)benzenesulfonamide

Combine 4-(trifluoromethyl)benzenesulfonamide (1.44g, 6.4mmol) and oxalyl chloride (15mL) and reflux for 9 hours. Evaporate the excess oxalyl chloride in vacuo to give the title compound.

Step c: [4-(Trifluoromethyl)benzenesulfonyl]isocyanate

Combine N-[(1-oxo-2-oxo-2-chloro)ethyl]-4-(trifluoromethyl)benzenesulfonamide (2g, 6.4mmol) and o-dichlorobenzene (25mL). Reflux for 16 hours then remove the solvent by fractional distillation (6mm Hg vacuum through a column packed with glass helices). Purify by distillation to give the title compound (1.15g, 72%); bp 62°–4° C.@0.075mm.

Step d: 5,7-Dichloro-4-[4-(trifluoromethyl)benzenesulfonimide]-1,4-dihydroquinoline-2-carboxylic acid, methyl ester Combine [4-(trifluoromethyl)benzenesulfonyl]isocyanate (1.15g, 4.5mmol), 5,7-dichloro-4-hydroxyquinoline-2-carboxylic acid, methyl ester (1.03g, 3.8mmol) and acetonitrile (8mL). Reflux for 16 hours, cool and filter to give the title compound as a yellow solid (1.47g, 81%); mp 252°–3° C. (acetonitrile).

Anal. Calcd for $C_{18}H_{11}Cl_2F_3N_2O_4S$: C, 45.11; H, 2.31; N, 5.85;
Found: C, 45.04; H, 2.23; N, 5.85.

EXAMPLE 2

5,7-Dichloro-4-[4-(trifluoromethyl)benzenesulfonimide]-1,4-dihydroquinoline-2-carboxylic acid

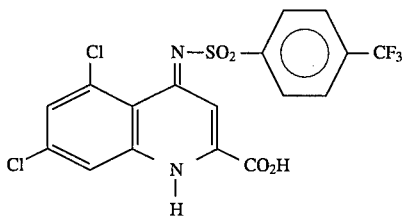

Combine 5,7-dichloro-4-[4-(trifluoromethyl)benzenesulfonimide]-1,4-dihydroquinoline-2-carboxylic acid, methyl ester (1.40g, 2.9mmol), lithium hydroxide hydrate (245mg, 5.8mmol), water (6mL) and methanol (30mL). Stir under a nitrogen atmosphere for 6 hours. Dilute with water (100mL) and adjust to pH 2 with 12N hydrochloric acid. Filter the light yellow solid, wash with water and dry to give the title compound as a lightly yellow solid (1.05g, 72%); mp 246°–7° C. (dec) (acetone/water).

Anal. Calcd for $C_{17}H_9Cl_2F_3N_2O_4S$: C, 43.89; H, 1.95; N, 6.02;
Found: C, 43.82; H, 1.76; N, 5.97.

EXAMPLE 3

5,7-Dichloro-4-[4-(fluoro)benzenesulfonimide]-1,4-dihydroquinilone-2-carboxylic acid, methyl ester

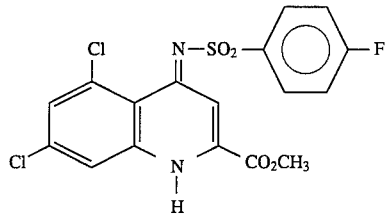

Step a: 4-(Fluoro)benzenesulfonamide

Combine 4-(fluoro)benzenesulfonyl chloride (6g, 0.03mol) and concentrated ammonium hydroxide (80mL). Seal and stir for 16 hours at room temperature. Heat at 90° C. to remove the ammonia and then add hydrochloric acid (1mL of a 12N solution). Cool, filter and dry to give the title compound as an off-white solid (4.4g, 85%); mp 124°–5° C. Anal. Calcd for $C_7H_6FNO_2S$: C, 41.13; H, 3.45; N, 8;
Found: C, 41.19; H, 3.39; N. 7.92.

Step b: N-[(1-Oxo-2-oxo-2-chloro)ethyl]-4-(fluoro)benzenesulfonamide

Combine 4-(fluoro)benzenesulfonamide (1.12g, 6.4mmol) and oxalyl chloride (15mL) and reflux for 9 hours. Evaporate the excess oxalyl chloride in vacuo to give the title compound.

Step c: [4-(Fluoro)benzenesulfonyl]isocyanate

Combine N-[(1-oxo-2-oxo-2-chloro)ethyl]-4-(fluoro)benzenesulfonamide (1.70g, 6.4mmol) and o-dichlorobenzene (25mL). Reflux for 16 hours then remove the solvent by fractional distillation (6mm Hg vacuum through a column packed with glass helices). Purify by distillation to give the title compound (1.15g, 32%); bp 80° C.@0.075mm.

Step d: 5,7-Dichloro-4-[4-(fluoro)benzenesulfonimide]-1,4-dihydroquinoline-2-carboxylic acid, methyl ester Combine [4-(fluoro)benzenesulfonyl]isocyanate (905mg, 4.5mmol), 5,7-dichloro-4-hydroxyquinoline-2-carboxylic acid, methyl ester (1.03g, 3.8mmol) and acetonitrile (8mL). Reflux for 16 hours, cool and filter to give the title compound as a yellow solid (1.56g, 83%); mp 234°–5° C.

EXAMPLE 4

5,7-Dichloro-4-[4-(fluoro)benzenesulfonimide]-1,4-dihydroquinoline-2-carboxylic acid

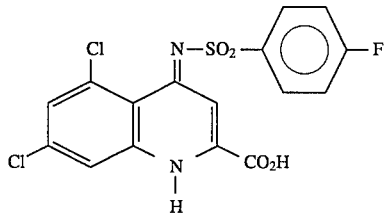

Combine 5,7-dichloro-4-[4-(fluoro)benzenesulfonimide]-1,4-dihydroquinoline-2-carboxylic acid, methyl ester (1.21g, 2.9mmol), lithium hydroxide hydrate (245mg, 5.8mmol), water (6mL) and methanol (30mL). Stir under a nitrogen atmosphere for 6 hours. Dilute with water (100mL) and adjust to pH 2 with 12N hydrochloric acid. Filter the light yellow solid, wash with water and dry to give the title compound (457mg, 39%); mp 225.5°–223° C. (dec).

Anal. Calcd for $C_{16}H_9Cl_2FN_2O_4S \cdot 1.1H_2O$: C, 44.17; H, 2.60; N, 6.44;
Found: C, 44.26; H. 2.41; N, 5.20.

EXAMPLE 5

5,7-Dichloro-4-[(2-thiophene)sulfonimide]-1,4-dihydroquinoline-2-carboxylic acid, methyl ester

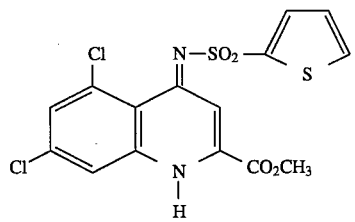

Step a: (2-Thiophene)sulfonamide
Combine 2-thiophenesulfonyl chloride (5g, 0.01mol) and concentrated ammonium hydroxide (80mL). Seal and stir for 16 hours at room temperature. Heat at 90° C. to remove the ammonia and then add hydrochloric acid (1mL of a 12N solution). Cool, filter and dry to give the title compound as an off-white solid (4g, 90%); mp 137°–8° C.
Anal. Calcd for: C, 29.43; H, 3.09; N, 8.58;
Found: C, 29.34; H, 2.97; N. 8.52.
Step b: N-[(1-Oxo-2-oxo-2-chloro)ethyl]-(2-thiophene)-sulfonamide
Combine (2-thiophene)sulfonamide (1.04g, 6.4mmol) and oxalyl chloride (15mL) and reflux for 9 hours. Evaporate the excess oxalyl chloride in vacuo to give the title compound.
Step c: [(2-Thiophene)sulfonyl]isocyanate
Combine N-[(1-oxo-2-oxo-2-chloro)ethyl]-(2-thiophene)-sulfonamide (1.63g, 6.4mmol) and o-dichlorobenzene (25mL). Reflux for 16 hours then remove the solvent by distillation (6mm Hg vacuum through a column packed with glass helices). Purify by distillation to give the title compound (680mg, 30%); bp 80°–90° C.@0.075mm.
Step d: 5,7-Dichloro-4-[(2-thiophene)sulfonimide]-1,4-dihydroquinoline-2-carboxylic acid, methyl ester
Combine [(2-thiophene)sulfonyl]isocyanate (680mg, 3.1mmol), 5,7-dichloro-4-hydroxyquinoline-2-carboxylic acid, methyl ester (0.85g, 3.6mmol) and acetonitrile (8mL). Reflux for 16 hours, cool and filter to give the title compound as a yellow solid (1.03mg, 80%); mp 215°–16° C.
Anal. Calcd for $C_{15}H_{10}Cl_2N_2O_4S$: C, 43.17; H, 2.42; N. 6.71;
Found: C, 43.21; H, 2.19; N, 6.73.

EXAMPLE 6

5,7-Dichloro-4-[(2-thiophene)sulfonimide]-1,4-dihydroquinoline-2-carboxylic acid

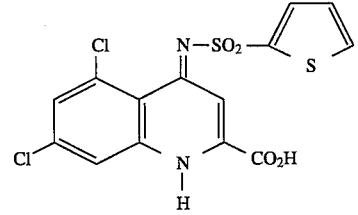

Combine 5,7-dichloro-4-[(2-thiophene)sulfonimide]-1,4-dihydroquinoline-2-carboxylic acid, methyl ester (0.93g, 2.2mmol), lithium hydroxide hydrate (187mg, 4.4mmol), water (4.5mL) and methanol (22mL). Stir under a nitrogen atmosphere for 6 hours. Dilute with water (100mL) and adjust to pH 2 with 12N hydrochloric acid. Filter the light yellow solid, wash with water and dry to give the title compound (0.80g, 91%); mp 156°–8° C. (dec).
Anal. Calcd for $C_{14}H_8Cl_2N_2O_4S \cdot H_2O$: C, 39.92; H, 2.39; N, 6.65;
Found: C, 39.95; H, 2.21; N, 6.70.

EXAMPLE 7

5,7-Dichloro-4-[4-(methoxy)benzenesulfonimide]-1,4-dihydroquinoline-2-carboxylic acid, methyl ester

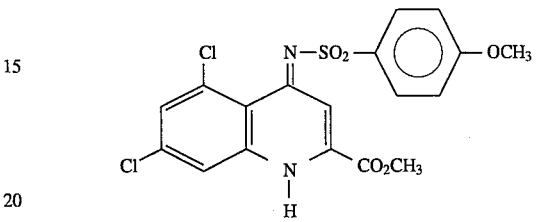

Step a: 4-(methoxy)benzenesulfonamide
Combine 4-(methoxy)benzenesulfonyl chloride (8.24g, 0.04mol) and concentrated ammonium hydroxide (80mL). Seal and stir for 16 hours at room temperature. Heat at 90° C. to remove the ammonia and then add hydrochloric acid (1mL of a 12N solution). Cool, filter and dry to give the title compound as an off-white solid (5.63g, 76%); mp 109°–10° C.
Step b: N-[(1-Oxo-2-oxo-2-chloro)ethyl]-4-(methoxy)benzenesulfonamide
Combine 4-(methoxy)benzenesulfonamide (1.20g, 6.4mmol) and oxalyl chloride (15mL) and reflux for 9 hours. Evaporate the excess oxalyl chloride in vacuo to give the title compound.
Step c: [4-(Methoxy)benzenesulfonyl]isocyanate
Combine N-[(1-oxo-2-oxo-2-chloro)ethyl]-4-(methoxy)-benzenesulfonamide (1.78g, 6.4mmol) and o-dichlorobenzene (25mL). Reflux for 16 hours then remove the solvent by distillation (6mm Hg vacuum through a column packed with glass helices). Purify by distillation to give the title compound (1.67g, 79%); bp 111°–12° C.@0.075mm.
Step d: 5,7-Dichloro-4-[4-(methoxy)benzenesulfonimide]-1,4-dihydroquinoline-2-carboxylic acid, methyl ester
Combine [4-(methoxy)benzenesulfonyl]isocyanate (1.06g, 7.8mmol), 5,7-dichloro-4-hydroxyquinoline-2-carboxylic acid, methyl ester (1.03g, 3.8mmol) and acetonitrile (8mL). Relfux for 16 hours, cool and filter to give the title compound as a yellow solid (1.56g, 91%); mp 224°–5° C.

EXAMPLE 8

5,7-Dichloro-4-[4-(methoxy)benzenesulfonimide]-1,4-dihydroquinoline-2-carboxylic acid

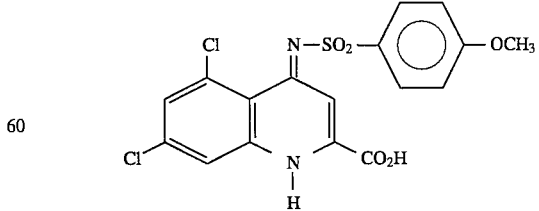

Combine 5,7-dichloro-4-[4-(methoxy)benzenesulfonimide]-1,4-dihydroquinoline-2-carboxylic acid, methyl ester (1.45g, 3.3mmol), lithium hydroxide hydrate (350mg, 8.2mmol), water (6mL) and methanol (30mL). Stir under a nitrogen atmosphere for 6 hours. Dilute with water (100mL) and adjust to pH 2 with 12N hydrochloric acid. Filter the light yellow solid, wash with water and dry to give the title compound (1.20g, 85%); mp 206°–8° C. (dec).

Anal. Calcd for $C_{17}H_{12}Cl_2N_2O_5S$: C, 47.79; H, 2.84; N, 6.76;

Found: C, 47.65; H, 2.84; N, 6.45.

EXAMPLE 9

5,7-Dichloro-4-[benzenesulfonimide]-1,4-dihydroquinoline-2-carboxylic acid, methyl ester

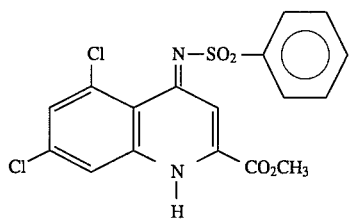

Combine benzenesulfonyl isocyanate (824mg, 4.5mmol), 5,7-dichloro-4-hydroxyquinoline-2-carboxylic acid, methyl ester (1.03g, 3.8mmol) and acetonitrile (8mL). Relfux for 16 hours, cool and filter to give the title compound as a yellow solid (1.67g, 93%); mp 218°–19° C.

EXAMPLE 10

5,7-Dichloro-4-[benzenesulfonimide]-1,4-dihydroquinoline-2-carboxylic acid

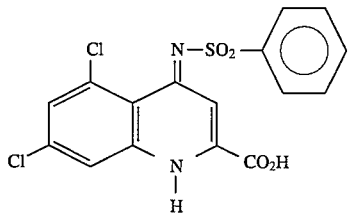

Combine 5,7-dichloro-4-[benzenesulfonimide]-1,4-dihydroquinoline-2-carboxylic acid, methyl ester (5.1g, 12mmol), lithium hydroxide hydrate (1.35mg, 32.2mmol), water (30mL) and methanol (900mL). Stir under a nitrogen atmosphere for 6 hours. Dilute with water (100mL) and adjust to pH 2 with 12N hydrochloric acid. Filter the light yellow solid, wash with water and dry to give the title compound (4.12g, 84%); mp 204°–5° C. (dec).

Anal. Calcd for $C_{16}H_{10}Cl_2N_2O_4S \cdot 3/8H_2O$: C, 47.58; H, 2.68; N, 6.94;

Found: C, 47.21; H, 2.56; N, 6.92.

EXAMPLE 11

5,7-Dichloro-4-[(4-methyl)benzenesulfonimide]-1,4-dihydroquinoline-2-carboxylic acid, methyl ester

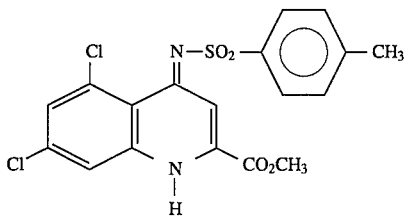

Combine p-toluenesulfonyl isocyanate (599mg, 4.5mmol), 5,7-dichloro-4-hydroxyquinoline-2-carboxylic acid, methyl ester (1.03g, 3.8mmol) and acetonitrile (8mL). Relfux for 16 hours, cool and filter to give the title compound as a yellow solid (1.79g, 96%); mp 217°–19° C.

Anal. Calcd for $C_{18}H_{14}Cl_2N_2O_4S$: C, 50.84; H, 3.32; N, 6.59;

Found: C, 50.81; H, 3.02; N, 6.38.

EXAMPLE 12

5,7-Dichloro-4-[(4-methyl)benzenesulfonimide]-1,4-dihydroquinoline-2-carboxylic acid

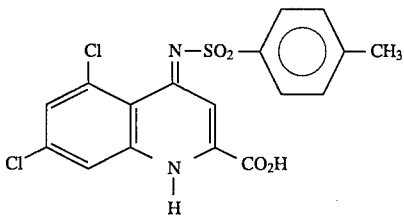

Combine 5,7-dichloro-4-[(4-methyl)benzenesulfonimide]-1,4-dihydroquinoline-2-carboxylic acid, methyl ester (1.20g, 2.9mmol), lithium hydroxide hydrate (245mg, 5.8mmol), water (6mL) and methanol (30mL). Stir under a nitrogen atmosphere for 6 hours. Dilute with water (100mL) and adjust to pH 2 with 12N hydrochloric acid. Filter the light yellow solid, wash with water and dry to give the title compound (1.07g, 92%); mp 308°–11° C. (dec).

MS (M+=411 with di-chloro pattern)

EXAMPLE 13

5,7-Dichloro-4-[(4-chloro)benzenesulfonimide]-1,4-dihydroquinoline-2-carboxylic acid, methyl ester

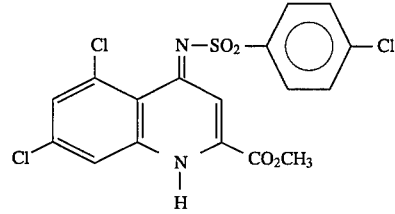

Combine 4-chlorobenzenesulfonyl isocyanate (693mg, 4.5mmol), 5,7-dichloro-4-hydroxyquinoline-2-carboxylic acid, methyl ester (1.03g, 3.8mmol) and propionitrile (8mL).

Relfux for 16 hours, cool and filter to give the title compound as a yellow solid (1.72g, 88%); mp 260°–62° C. (dec).
Anal. Calcd for $C_{17}H_{11}Cl_3N_2O_4S$: C, 45.81; H, 2.49; N, 6.29;
Found: C, 45.76; H, 2.29; N, 6.28.

EXAMPLE 14

5,7-Dichloro-4-[(4-chloro)benzenesulfonimide]-1,4-dihydroquinoline-2-carboxylic acid

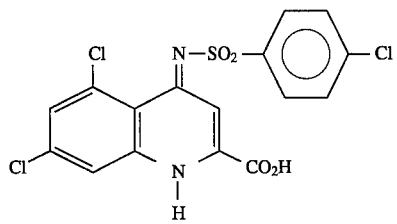

Combine 5,7-dichloro-4-[(4-chloro)benzenesulfonimide]-1,4-dihydroquinoline-2-carboxylic acid, methyl ester (1.26g, 2.9mmol), lithium hydroxide hydrate (245mg, 5.8mmol), water (6mL) and methanol (30mL). Stir under a nitrogen atmosphere for 6 hours. Dilute with water (100mL) and adjust to pH 2 with 12N hydrochloric acid. Filter the light yellow solid, wash with water and dry to give the title compound (1.22g, 100%); mp 295°–8° C.
MS (M+=431 with tri-chloro pattern)

EXAMPLE 15

5,7-Dichloro-4-[trifluoromethylsulfonimide]-1,4-dihydroquinolinebenzene-2-carboxylic acid, methyl ester

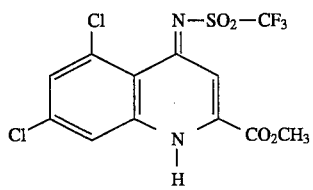

Combine trifluoromethylsulfonyl isocyanate (788mg, 4.5mmol), 5,7-dichloro-4-hydroxyquinoline-2-carboxylic acid, methyl ester (1.03g, 3.8mmol) and acetonitrile (8mL). Relfux for 16 hours, cool and filter to give the title compound; mp 265°–6° C. (dec).
Anal. Calcd for $C_{12}H_7Cl_2F_3N_2O_4S$: C, 35.75; H, 1.75; N, 6.95;
Found: C, 35.72; H, 1.57; N, 6.87.

EXAMPLE 16

5,7-Dichloro-4-[trifluoromethylsulfonimide]-1,4-dihydroquinoline-2-carboxylic acid

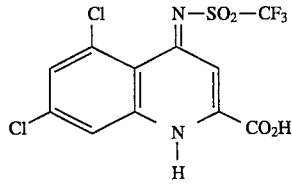

Combine 5,7-dichloro-4-[trifluoromethylsulfonimide]-1,4-dihydroquinoline-2-carboxylic acid, methyl ester (1.14g, 2.9mmol), lithium hydroxide hydrate (245mg, 5.8mmol), water (6mL) and methanol (30mL). Stir under a nitrogen atmosphere for 6 hours. Dilute with water (100mL) and adjust to pH 2 with 12N hydrochloric acid. Filter, wash with water and dry to give the title compound.

EXAMPLE 17

5-Ethyl-7-bromo-4-[benzenesulfonimide]-1,4-dihydroquinoline-2-carboxylic acid, ethyl ester

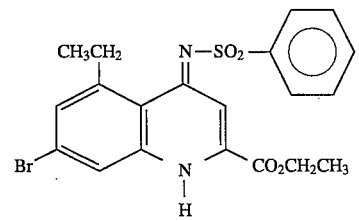

Mix 4-ethyl-2-nitroaniline (16.6g, 0.1mol) in water (400mL) and add 48% hydrobromic acid (1kg). Add bromine (16g, 0.1mol) with stirring and stir for 1 hour. Dilute to 2L and cool to 7° C. Filter, wash with water and dry to give 4-ethyl-2-nitro-6-bromoaniline.
Dissolve 4-ethyl-2-nitro-6-bromoaniline (6.62g, 27mmol) in ethanol (40mL). Add, by dropwise addition, concentrated sulfuric acid (5mL) and heat at reflux, adding sodium nitrite (4.55g, mmol) in small portions over 25 minutes. Stir at room temperature for several hours, pour onto ice and extract into ethyl acetate. Wash with water (3×) and brine (3×). Dry (MgSO$_4$) and evaporate the solvent in vacuo and purify by silica gel chromatography to give 3-bromo-5-ethylnitrobenzene.
Dissolve 3-bromo-5-ethylnitrobenzene (6.21g, 27mmol) in acetic acid (40mL) and ethanol (30mL) and treat with iron powder (2.7g). Reflux for 3 hours, filter through Celite and evaporate the solvent in vacuo. Purify by silica gel chromatography to give 3-bromo-5-ethylaniline.
Dissolve 3-bromo-5-ethylaniline (4.7g, 23.5mmol) in methanol (100mL) and add diethylacetylene dicarboxylate (5.5mL) at room temperature. Reflux for 10 hours and cool to room temperature. Evaporate the solvent in vacuo and add to diphenylether (100mL) at 250° C. Stir for 15 minutes and let cool to room temperature. Add hexane (500mL) and filter the precipitate. Purify by silica gel chromatography to give 5-ethyl-7-bromo-4-oxo-1,4-dihydroquinoline-2-carboxylic acid, ethyl ester
Combine benzenesulfonyl isocyanate (824mg, 4.5mmol), 5-ethyl-7-bromo-4-oxo-1,4-dihydroquinoline-2-carboxylic acid, ethyl ester (1.23g, 3.8mmol) and acetonitrile (8mL). Relfux for 16 hours, cool and filter to give the title compound.

EXAMPLE 18

5-Ethyl-7-bromo-4-[benzenesulfonimide]-1,4-dihydroquinoline-2-carboxylic acid

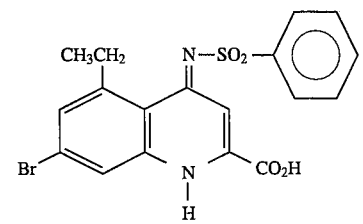

Combine 5-ethyl-7-bromo-4-[benzenesulfonimide]-1,4-dihydroquinoline-2-carboxylic acid, ethyl ester (1.34g, 2.9mmol), lithium hydroxide hydrate (245mg, 5.8mmol), water (6mL) and methanol (30mL). Stir under a nitrogen atmosphere for 6 hours. Dilute with water (100mL) and adjust to pH 2 with 12N hydrochloric acid. Filter to give the title compound.

EXAMPLE 19

5-Bromo-7-fluoro-4-[benzenesulfonimide]-1,4-dihydroquinoline-2-carboxylic acid, methyl ester

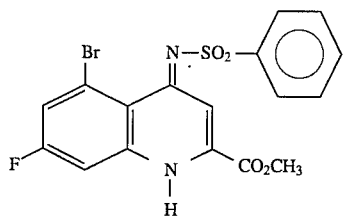

Mix water (1800mL), 48% hydrobromic acid (3000mL) and 4-fluoro-2-nitroaniline (75g, 0.48mol) 4-fluoro-2-nitro-6-bromoaniline. Cool to 25° C. and add, by dropwise addition over 30 minutes, bromine (78.6g, 0.48mmol). Stir at room temperature for 45 minutes and dilute with ice-water (4200mL) to cool to 5° C. Filter, wash with water and dry ($P_2O_5$) to give 4-fluoro-2-nitro-6-bromoaniline (107.2g, 95%); mp 71.5°–72.5° C.
Anal. Calcd for $C_6H_4BrFN_2O_2$: C, 30.66; H, 1.72; N, 11.92; Found: C, 30.68; H, 1.74; N, 11.53.
Mix water (60mL), concentrated sulfuric acid (60mL) and 4-fluoro-2-nitro-6-bromoaniline (9.65g, 41mmol). Cool to 0° C. and add solid sodium nitrite (4.25g, 61mmol) in small portions at such a rate as not to exceed 5° C. Stir for 30 minutes and add ferrous sulfate heptahydrate (5.6g, 20.5mmol) and ethanol (18mL). Stir with warming to room temperature over 2 hours. Add water (200mL), separate the organic phase and wash the aqueous phase with methylene chloride (2×). Combine the organic phases, dry ($MgSO_4$) and evaporate the solvent in vacuo. Purify by silica gel chromatography (5% ethyl acetate/hexane) give 3-bromo-5-fluoronitrobenzene (4.5g); bp 65°–70° C.@1.0mm Hg.
Anal. Calcd for $C_5H_3BrFNO_2$: C, 32.75; H, 1.37; N, 6.37; Found: C, 32.67; H, 1.27; N, 6.16.
Mix methanol (17mL) and 12N hydrochloric acid (18mL) and add iron powder (5.34g, 95mmol) until the mixture refluxes. Stir and allow to come to room temperature. Add water (200mL) and separate the organic phase. Wash the aqueous phase with methylene chloride (2×), combine the organic phases and dry ($MgSO_4$). Evaporate the solvent in vacuo and purify by silica gel chromatography (10% ethyl acetate/hexane) and distill to give to give 3-fluoro-5-bromoaniline; bp 85°–90° C.@0.5mm Hg.
Anal. Calcd for $C_6H_5BrFN$: C, 37.92; H, 2.65; N, 7.37; Found: C, 37.87; H, 2.54; N, 7.35.
Combine 3-fluoro-5-bromoaniline (5.0g, 26.3mmol), dimethylacetylene dicarboxylate (3.25mL) and methanol (150mL). Heat at reflux for 3 hours, cool to room temperature and stir for 3 days. Evaporate the solvent in vacuo purify by silica gel chromatography (10% ethyl acetate/hexane) to give 3-fluoro-5-bromo-N-(dimethylfumaryl)aniline (0.48g).
Anal. Calcd for $C_{12}H_{11}BrFNO_4$: C, 43.39; H, 3.34; N, 4.22; Found: C, 42.97; H, 3.02; N, 3.98.
Mix 3-fluoro-5-bromo-N-(dimethylfumaryl)aniline (7.8g, 23mmol) and diphenyl ether (117g). Heat at reflux for 20 minutes. Add hexane (800mL) and filter. Purify by silica gel chromatography (40% ethyl acetate/hexane) and crystallize (acetonitrile) to give 5-bromo-7-fluoro-4-oxo-1,4-dihydroquinoline-2-carboxylic acid, methyl ester; mp 289°–289.5° C. (dec).
Anal. Calcd for $C_{11}H_7BrFNO_3$: C, 44.02; H, 2.35, N, 4.67; Found: C, 44.18; H, 2.26; N, 4.55.
Combine benzenesulfonyl isocyanate (824mg, 4.5mmol), 5-bromo-7-fluoro-4-oxo-1,4-dihydroquinoline-2-carboxylic acid, methyl ester (1.14g, 3.8mmol) and acetonitrile (8mL). Reflux for 16 hours, cool and filter to give the title compound.

EXAMPLE 20

5-Bromo-7-fluoro-4-[benzenesulfonimide]-1,4-dihydroquinoline-2-carboxylic acid

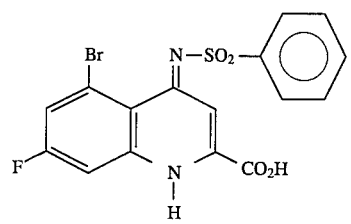

Combine 5-bromo-7-fluoro-4-[benzenesulfonimide]-1,4-dihydroquinoline-2-carboxylic acid, ethyl ester (1.23g, 2.9mmol), lithium hydroxide hydrate (245mg, 5.8mmol), water (6mL) and methanol (30mL). Stir under a nitrogen atmosphere for 6 hours. Dilute with water (100mL) and adjust to pH 2 with 12N hydrochloric acid. Filter to give the title compound.

EXAMPLE 21

5,7-Dichloro-4-[2-chlorobenzenesulfonimide]-1,4-dihydroquinoline-2-carboxylic acid, methyl ester

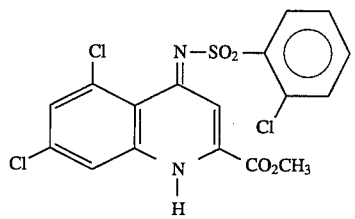

Combine [2-chlorobenzenesulfonyl]isocyanate (10g, 46mmol), 5,7-dichloro-4-hydroxyquinoline-2-carboxylic acid, methyl ester (5g, 18mmol) and acetonitrile (36mL). Reflux for 4 hours, cool and filter. Recrystallize (acetonitrile) to give the title compound (7.1g, 87%); mp 219.5°–220.5° C.
Anal. Calcd for $C_{17}H_{11}Cl_3N_2O_4S$: C, 45.81; H, 2.49; N, 6.29;
Found: C, 45.79; H, 2.67; N, 6.44.

EXAMPLE 22

5,7-Dichloro-4-[2-chlorobenzenesulfonimide]-1,4-dihydroquinoline-2-carboxylic acid

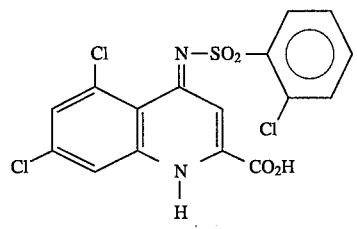

Combine water (9mL), methanol (45mL), lithium hydroxide hydrate (0.47g, 11.2mmol) and 5,7-dichloro-4-[2-chlorobenzenesulfonimide]-1,4-dihydroquinoline-2-carboxylic acid, methyl ester (2g, 4.5mmol). Seal and stir overnight. Evaporate the methanol in vacuo and dilute with water (100mL). Adjust to pH2 with 12N hydrochloric acid, filter and wash with water. Crystallize (acetone/water) to give the title compound (1.62g, 83%); mp 226.5°–228° C. (dec).
Anal. Calcd for $C_{16}H_9Cl_3N_2O_4S$: C, 44.51; H, 2.10; N, 6.49; Found: C, 44.28; H, 2.29; N, 6.09.

EXAMPLE 23

5,7-Dichloro-4-[3-chlorobenzenesulfonimide]-1,4-dihydroquinoline-2-carboxylic acid, methyl ester

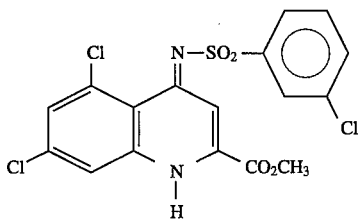

Combine oxalyl chloride (25mL) and 3-chlorobenzenesulfonamide (4.3g, 23mmol) and reflux overnight. Remove oxalyl chloride in vacuo and combine the resulting residue with o-dichlorobenzene (25mL) and reflux. Evaporate the solvent in vacuo to distill to give [3-chlorobenzenesulfonyl] isocyanate (2g, 40%); bp 92°–5° C.
Combine [3-chlorobenzenesulfonyl]isocyanate (2g, 9.2mmol), 5,7-dichloro-4-hydroxyquinoline-2-carboxylic acid, methyl ester (1.67g, 6.1mmol) and acetonitrile (2mL). Reflux overnight, add methanol and stir for 1 hour at room temperature. Adsorb onto silica gel and purify by silica gel chromatography (10% ethyl acetate/hexane) and recrystallize (acetonitrile) to give the title compound (0.74g, 27%); mp 248°–58° C.
Anal. Calcd for $C_{17}H_{11}Cl_3N_2O_4S$: C, 45.81; H, 2.49; N, 6.29;
Found: C, 45.91; H, 2.61; N, 6.11.

EXAMPLE 24

5,7-Dichloro-4-[3-chlorobenzenesulfonimide]-1,4-dihydroquinoline-2-carboxylic acid

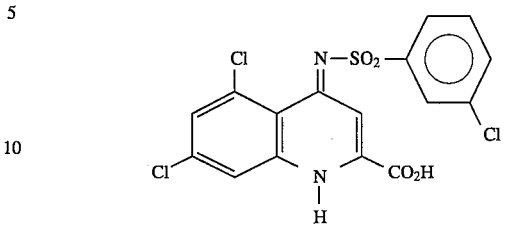

Combine water (4mL), methanol (12mL), lithium hydroxide hydrate (0.17g, 4mmol) and 5,7-dichloro-4-[3-chlorobenzenesulfonimide]-1,4-dihydroquinoline-2-carboxylic acid, methyl ester (0.6g, 1.3mmol). Stir for 4 hours at room temperature, dilute with water (100mL) and adjust to pH2 with 12N hydrochloric acid. Filter and recrystallize (acetone/water) to give the title compound (0.47g, 84%); mp 210°–11° C. (dec).
Anal. Calcd for $C_{16}H_9Cl_3N_2O_4S$: C, 44.51; H, 2.10; N, 6.49; Found: C, 44.42; H, 2.22; N, 6.21.

The following compounds can be prepared analogously to those described in Examples 1–24:
5,7-dichloro-4-[4-(hydroxy)benzenesulfonimide]-1,4-dihydroquinoline-2-carboxylic acid;
5,7-Dibromo-4-[benzenesulfonimide]-1,4-dihydroquinoline-2-carboxylic acid;
5-Bromo-7-chloro-4-[benzenesulfonimide]-1,4-dihydroquinoline-2-carboxylic acid;

The compounds of Formula I wherein X is represented by a phenyl derivative, A is represented by a substituent selected from the group consisting of hydrogen, OH, halogen, CN, $NO_2$, $C_1$–$C_6$ alkyl, $C_1$–$C_6$ alkoxy, $OCF_3$, $CF_3$ and B is a group represented $NH(CO)OR_3$ and D is represented by $C(O)OR_1$, wherein $R_1$ is $C_1$–$C_6$ alkyl or $C(O)NR_1R_2$ wherein $R_1$ and $R_2$ are as previously defined, the compounds of Formula I wherein X is represented by a phenyl derivative, A is represented by a substituent selected from the group consisting of hydrogen, OH, halogen, CN, $NO_2$, $C_1$–$C_6$ alkyl, $C_1$–$C_6$ alkoxy, $OCF_3$, $CF_3$, B is a group represented $NHC(O)R_3$, $NHC(O)NHR_3$, $NHSO_2CF_3$, or $NHSO_2C_6H_5$ and D is represented by $C(O)OR_1$, wherein $R_1$ is hydrogen and the compounds of Formula I wherein X is represented by a phenyl derivative, A is represented by a substituent selected from the group consisting of hydrogen, OH, halogen, CN, $NO_2$, $C_1$–$C_6$ alkyl, $C_1$–$C_6$ alkoxy, $OCF_3$, $CF_3$, B is a group represented $NH_2$ and D is represented by $C(O)OR_1$, wherein $R_1$ is hydrogen may be prepared using techniques and procedures well known and appreciated by one of ordinary skill in the art. A general synthetic procedure for preparing these compounds is set forth in Scheme B. In Scheme B, all substituents unless otherwise indicated are as previously defined.

Scheme B

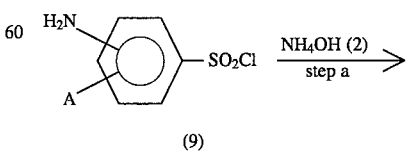

(9)

-continued
Scheme B

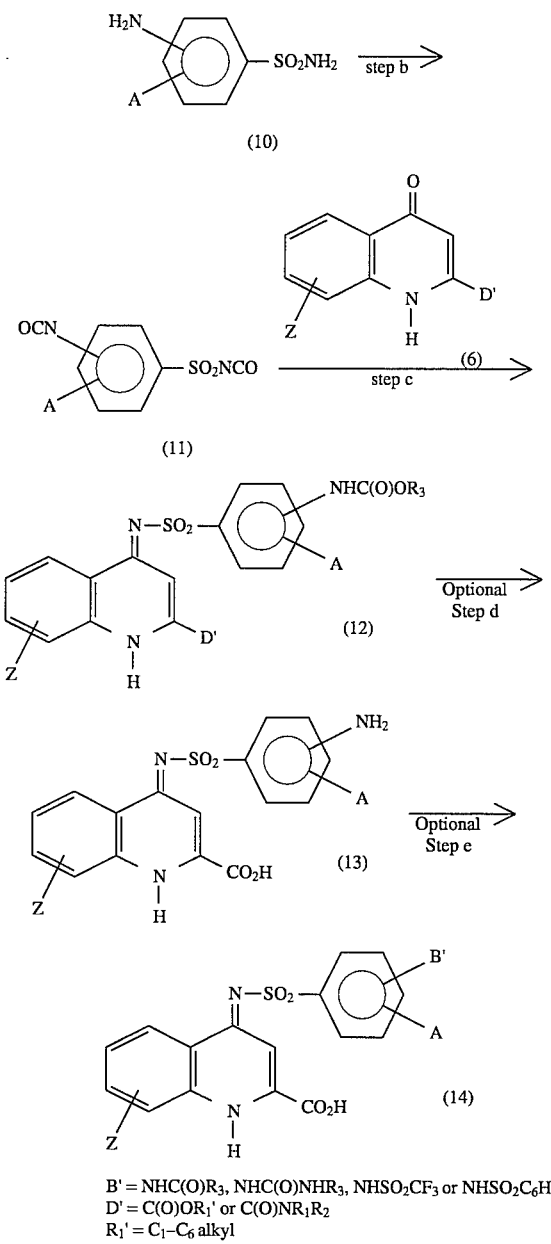

B' = NHC(O)R$_3$, NHC(O)NHR$_3$, NHSO$_2$CF$_3$ or NHSO$_2$C$_6$H$_5$
D' = C(O)OR$_1$' or C(O)NR$_1$R$_2$
R$_1$' = C$_1$-C$_6$ alkyl Scheme B provides a general synthetic scheme for preparing the compounds of Formula I wherein X is represented by a phenyl derivative, A is represented by a substituent selected from the group consisting of hydrogen, OH, halogen, CN, NO$_2$, C$_1$-C$_6$ alkyl, C$_1$-C$_6$ alkoxy, OCF$_3$, CF$_3$, B is a group represented NH(CO)OR$_3$ and D is represented by C(O)OR$_1$, wherein R$_1$ is C$_1$-C$_6$ alkyl or C(O)NR$_1$R$_2$ wherein R$_1$ and R$_2$ are as previously defined, the compounds of Formula I wherein X is represented by a phenyl derivative, A is represented by a substituent selected from the group consisting of hydrogen, OH, halogen, CN, NO$_2$, C$_1$-C$_6$ alkyl, C$_1$-C$_6$ alkoxy, OCF$_3$, CF$_3$, B is a group represented NHC(O)R$_3$, NH(CO)OR$_3$, NHC(O)NHR$_3$, NHSO$_2$CF$_3$, or NHSO$_2$C$_6$H$_5$ and D is represented by C(O)OR$_1$, wherein R$_1$ is hydrogen and the compounds of Formula I wherein X is represented by a phenyl derivative, A is represented by a substituent selected from the group consisting of hydrogen, OH, halogen, CN, NO$_2$, C$_1$-C$_6$ alkyl, C$_1$-C$_6$ alkoxy, OCF$_3$, CF$_3$, B is a group represented NH$_2$ and D is represented by C(O)OR$_1$, wherein R$_1$ is hydrogen.

In step a, the appropriate aminobenzenesulfonyl chloride of structure (9) is amidated with ammonium hydroxide (2) to give the corresponding aminobenzene sulfonamide of structure (10) as described previously in Scheme A, step a.

In step b, both sulfonamide and amino functionalities of the appropriate aminobenzene sulfonamide of structure (10) are converted to the corresponding (isocyanato)benzenesulfonyl isocyanate of structure (11).

For example, the appropriate aminobenzenesulfonamide of structure (10) is contacted with a molar excess of either phosgene, triphosgene or oxalyl chloride, phosgene being preferred. The reactants are typically contacted in a suitable organic solvent such as nitrobenzene. The reactants are typically stirred together at a temperature range of from -10° C. to reflux and for a period of time ranging from 5-24 hours. The (isocyanato)benzenesulfonyl isocyanate of structure (11) is recovered from the reaction zone by evaporation of the volatiles.

In step c, the appropriate (isocyanato)benzenesulfonyl isocyanate of structure (11) is first reacted with an appropriate 4-oxo-1,4-dihydroquinoline of structure (6) to give the intermediate 4-[(isocyanato)benzenesulfonimide]-1,4-dihydroquinoline. The isocyanato functionality of the intermediate 4-(isocyanato)benzene)sulfonimide-1,4-dihydroquinoline is then decomposed by the addition of an appropriate alcohol of the formula R$_3$OH to give the corresponding 4-[(alkylcarbamoyl)benzenesulfonimide]-1,4-dihydroquinoline of structure (12).

For example, the appropriate (isocyanato)benzenesulfonyl isocyanate of structure (11) is contacted with a slight molar deficiency of an appropriate 4-oxo-1,4-dihydroquinoline of structure (6). The reactants are typically contacted in a polar anhydrous organic solvent such as acetonitrile or propionitrile. The reactants are typically stirred together for a period of time ranging from 4-24 hours and at a temperature range of from room temperature to reflux. The intermediate 4-[(isocyanato)benzenesulfonimide]-1,4-dihydroquinoline is recovered from the reaction zone by filtration. The intermediate 4-[(isocyanato)benzenesulfonimide]-1,4-dihydroquinoline is then treated with a molar excess of the appropriate alcohol of the formula R$_3$OH. The reactants are typically stirred together at reflux temperature for a period of time ranging from 2-24 hours. The 4-[(alkylcarbamoyl)benzenesulfonimide]-1,4-dihydroquinoline of structure (12) is recovered from the reaction zone by filtration. It may be purified by recrystallization as is known in the art.

Alternatively, the isocyanato functionality of the appropriate intermediate 4-[(isocyanato)benzenesulfonimide]-1,4-dihydroquinoline may be decomposed by the addition of an appropriate amine of the formula H$_2$NR$_3$ to give the corresponding 4-[(ureido)benzenesulfonimide]-1,4-dihydroquinoline of structure (14).

In optional step d, both the carbamoyl functionality and the ester or amide functionality of the appropriate 4-[(alkylcarbamoyl)benzenesulfonimide]-1,4-dihydroquinoline of structure (12) are hydrolyzed with a base such as sodium hydroxide to give the corresponding 4-[(amino)benzenesulfonimide]-1,4-dihydroquinoline-2-carboxylic acid of structure (13) as described previously in Scheme A, optional step e.

The 4-[(amino)benzenesulfonimide]-1,4-dihydroquinoline-2-carboxylic acid of structure (13) wherein A is a group represented by C(O)OR$_1$ wherein R$_1$ is C$_1$-C$_4$ alkyl, or C(O)NR$_1$R$_2$ can be prepared as described later in Scheme D, step a and optional step b$_1$ or optional step b$_2$.

In optional step e, the amino functionality of the appropriate 4-[(amino)benzenesulfonimide]-1,4-dihydroquinoline of structure (13) can be functionalized to give either the corresponding 4-[(amido)benzenesulfonimide]-1,4-dihydroquinoline of structure (14), 4-[(ureido)benzenesulfonimide]-1,4-dihydroquinoline of structure (14), 4-[(trifluoromethanesulfonamido)benzenesulfonimide]-1,4-dihydroquinoline of structure (14) or 4-[(benzenesulfonamido)benzenesulfonimide]-1,4-dihydroquinoline of structure (14).

For example, the appropriate 4-[(amino)benzenesulfonimide]-1,4-dihydroquinoline of structure (13) can be acylated to give the corresponding 4-[(amido)benzenesulfonimide]-1,4-dihydroquinoline of structure (14).

For example, the appropriate 4-[(amino)benzenesulfonimide-]-1,4-dihydroquinoline of structure (13) is contacted with a molar equivalent of the appropriate acylating agent represented by the formula $R_3COCl$. The reactants are typically contacted in a suitable non-nucleophilic organic base such as pyridine or an aqueous solvent such as dioxane/water buffered to pH 10 with a base such as sodium hydroxide. The reactants are typically stirred together at room temperature for a period of time ranging from 2–24 hours. The 4-[(amido)benzenesulfonimide]-1,4-dihydroquinoline of structure (14) is recovered from the reaction zone by extractive methods as is known in the art.

Similarly, the appropriate 4-[(amino)benzenesulfonimide]-1,4-dihydroquinoline of structure (13) can be converted to the corresponding 4-[(ureido)benzenesulfonimide]-1,4-dihydroquinoline of structure (14).

For example, the appropriate 4-[(amino)benzenesulfonimide]-1,4-dihydroquinoline of structure (13) is contacted with a molar equivalent of the appropriate isocyante of the formula $R_3NCO$. The reactants are typically contacted in a suitable organic solvent such as tetrahydrofuran. The reactants are typically stirred together at room temperature for a period of time ranging from 1–5 hours. The 4-[(ureido)benzenesulfonimide]-1,4-dihydroquinoline of structure (14) is recovered from the reaction zone by extractive methods as is known in the art.

In addition, the appropriate 4-[(amino)benzenesulfonimide]-1,4-dihydroquinoline of structure (13) can be converted to the corresponding 4-[(trifluoromethanesulfonamido)-benzenesulfonimide]-1,4-dihydroquinoline of structure (14) or 4-[(benzenesulfonamido)benzenesulfonimide]-1,4-dihydroquinoline of structure (14).

For example, the appropriate 4-[(amino)benzenesulfonimide]-1,4-dihydroquinoline of structure (13) is contacted with a molar excess of trifluoromethanesulfonic anhydride, and a molar excess of a base such as diisopropylethylamine. The reactants are typically contacted in methylene chloride. The reactants are typically stirred together for a period of time ranging from 2–24 hours and at a temperature range of from −78° C. to 85° C. The 4-[(trifluoromethanesulfonamido)benzenesulfonimide]-1,4-dihydroquinoline of structure (14) is recovered from the reaction zone by extractive methods as is known in the art. Similarly, the appropriate 4-[(amino)benzenesulfonimide]-1,4-dihydroquinoline of structure (13) is converted to the corresponding 4-[(benzenesulfonamido)benzenesulfonimide]-1,4-dihydroquinoline of structure (14) using benzenesulfonyl chloride instead of trifluoromethanesulfonic anhydride.

Starting materials for use in Scheme B are readily available to one of ordinary skill in the art. For example, p-isocyanatobenzenesulfonyl isocyanate is described in *J. Org. Chem.*, 30 1260–2 1965 and certain substituted aminobenzene sulfonamides of structure (10) are described in *Arzneim.-Forsch./Drug Res.* 28(8) 1331–4 1978, *J. Med. Chem.* 21(9) 845 1978, *Gazz. Chim. Ital.* 78 275 1948 and *J. Pharm. Parmacol.* 12 705 1960.

The following examples present typical syntheses as described in Scheme B. These examples are understood to be illustrative only and are not intended to limit the scope of the present invention in any way.

EXAMPLE 25

5,7-Dichloro-4-[4-(methylcarbamoyl)benzenesulfonimide]-1,4-dihydroquinoline-2-carboxylic acid, methyl ester

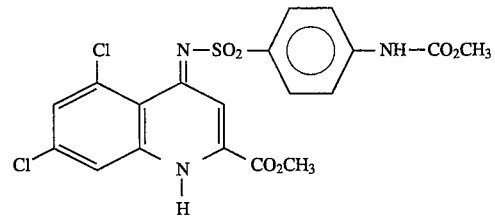

Combine 4-isocyanatobenzenesulfonyl isocyanate (45.8g, 0.2mol), 5,7-dichloro-4-hydroxyquinoline-2-carboxylic acid, methyl ester (27.2g, 0.1mol) and acetonitrile (400mL). Relfux for 4 hours, cool and add methanol (120mL) and reflux for several hours. Cool, filter and wash with acetonitrile. Triturate with boiling methanol (3L) by stirring at reflux for 1 hour. Cool while continuing to stir and collect the solid by filtration to give title compound (40.6g, 84%); mp 251.1°–252.5° C.

Anal. Calcd for $C_{19}H_{15}Cl_2N_3O_6S$: C, 47.12; H, 3.12; N, 8.67;

Found: C, 46.96; H, 3.09; N, 8.76.

EXAMPLE 26

5,7-Dichloro-4-[4-(ethylcarbamoyl)benzenesulfonimide]-1,4-dihydroquinoline-2-carboxylic acid, methyl ester

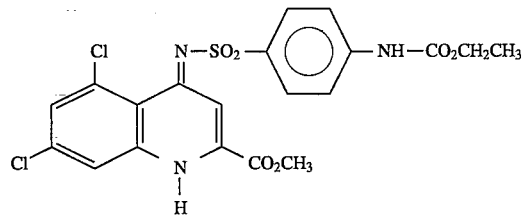

Combine 4-isocyanatobenzenesulfonyl isocyanate (4.9g, 0.021mol), 5,7-dichloro-4-hydroxyquinoline-2-carboxylic acid, methyl ester (3.3g, 0.012mol) and acetonitrile (50mL). Relfux for 2.5 hours, cool and add ethanol (25mL) and reflux for several hours. Cool and evaporate the solvent in vacuo. Triturate with boiling methanol (1.6L) by stirring at reflux for 1 hour. Cool while continuing to stir and collect the solid by filtration to give the title compound (5.5g, 92%); mp 256°–257° C.

Anal. Calcd for $C_{20}H_{17}Cl_2N_3O_6S$: C, 48.20; H, 3.44; N, 8.43;

Found: C, 48.21; H, 3.39; N, 8.36.

EXAMPLE 27

5,7-Dichloro-4-[4-(butylcarbamoyl)benzenesulfonimide]-1,4-dihydroquinoline-2-carboxylic acid, methyl ester

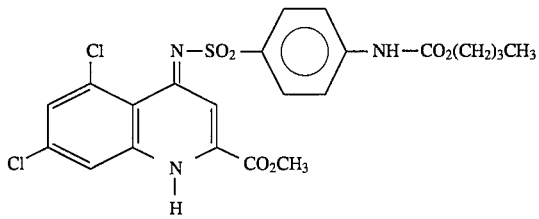

Combine 4-isocyanatobenzenesulfonyl isocyanate (4.9g, 0.021mol), 5,7-dichloro-4-hydroxyquinoline-2-carboxylic acid, methyl ester (3.3g, 0.012mol) and acetonitrile (50mL). Relfux for 2.5 hours, cool and add butanol (25mL) and reflux for several hours. Cool and evaporate the solvent in vacuo. Recrystalize (methanol, 1L) collect the solid by filtration to give the title compound (4.14g, 66%); mp 219°–220° C.
Anal. Calcd for $C_{22}H_{21}Cl_2N_3O_6S$: C, 50.19; H, 4.02; N, 7.98;
Found: C, 50.16; H, 4.01; N, 7.85.

EXAMPLE 28

5,7-Dichloro-4-[4-(methylureido)benzenesulfonimide]-1,4-dihydroquinoline-2-carboxylic acid, methyl ester

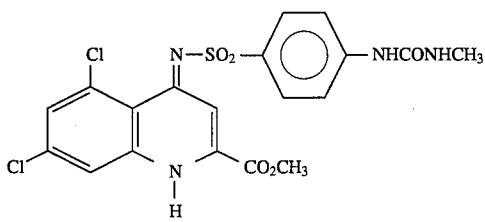

Combine 4-isocyanatobenzenesulfonyl isocyanate (4.9g, 0.021mol), 5,7-dichloro-4-hydroxyquinoline-2-carboxylic acid, methyl ester (3.3g 0.012mol) and acetonitrile (50mL). Relfux for 2.5 hours, cool to 0° C. and add 40% aqueous methylamine (10mL) and stir at room temperature for several hours. Evaporate the solvent in vacuo and triturate with methanol. Collect the solid by filtration and dissolve in 1600 ml of methanol/water 1/1, add 30 ml 1N HCl, 400 ml of water and cool to 0° C. Collect the solid by filtration to give title compound (2.40g, 41%); mp 250°–2° C. (dec).
Anal. Calcd for $C_{19}H_{16}Cl_2N_4O_5S$: C, 47.21; H, 3.34; N, 11.59;
Found: C, 47.17; H, 3.35; N, 11.62.

EXAMPLE 29

5,7-Dichloro-4-[4-aminobenzenesulfonimide]-1,4-dihydroquinoline-2-carboxylic acid

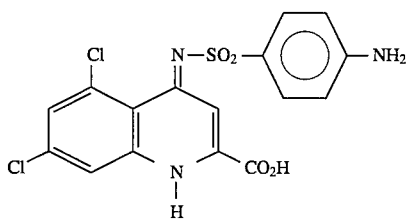

Combine 5,7-dichloro-4-[4-(methylcarbamoyl)benzenesulfonimide]-1,4-dihydroquinoline-2-carboxylic acid, methyl ester (378mg, 0.78mmol), sodium hydroxide (0.94g, 2.3mmol), water (1.4mL), and methanol (6mL). Stir at reflux temperature under a nitrogen atmosphere for 36 hours. Remove solvent in vacuo and dilute with water (100mL). Adjust to pH 2 with 12N hydrochloric acid. Filter to give the title compound; mp 178°–180.5° C. (dec) (acetone/water).
Anal. Calcd for $C_{16}H_{11}Cl_2N_3O_4S\cdot 0.75H_2O$: C, 45.12; H, 2.96; N, 9.87;
Found: C, 45.11; H, 2.97; N. 9.97.

EXAMPLE 30

5,7-Dichloro-4-[4-(methylcarbamoyl)-3-chlorobenzenesulfonimide]-1,4-dihydroquinoline-2-carboxylic acid, methyl ester

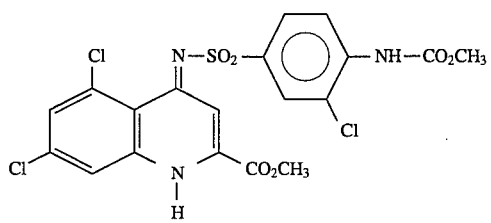

Dissolve 4-amino-3-chlorobenzenesulfonamide (0.96g, 5mmol) in chlorobenzene (10% solution) and distill the mixture to remove any traces of water. Cool to 100° C. and add n-butyl isocyanate (99mg, 1mmol). Heat to reflux and add, by dropwise addition, oxalyl chloride (1.5mL). Purge with nitrogen at 130°–132° C. for 30 minutes and distill to give 3-chloro-4-isocyanatobenzenesulfonyl isocyanate.
Combine 3-chloro-4-isocyanatobenzenesulfonyl isocyanate (52mg, 0.2mmol), 5,7-dichloro-4-hydroxyquinoline-2-carboxylic acid, methyl ester (27.2mg, 0.1mmol) and acetonitrile (40mL). Relfux for 4 hours and add methanol (12mL) and reflux for several hours. Cool, filter and wash with acetonitrile. Triturate with boiling methanol (3mL) by stirring at reflux for 1 hour. Cool while continuing to stir and collect the solid by filtration to give title compound.

EXAMPLE 31

5,7-Dichloro-4-[4-(methylcarbamoyl)-2-chlorobenzenesulfonimide]-1,4-dihydroquinoline-2-carboxylic acid, methyl ester

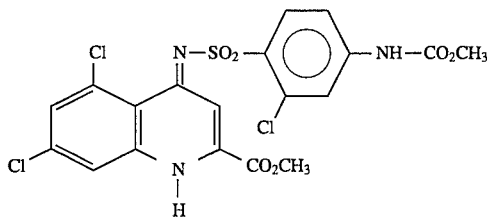

Dissolve 4-amino-2-chlorobenzenesulfonamide (0.96g, 5mmol) in chlorobenzene (10% solution) and distill the mixture to remove any traces of water. Cool to 100° C. and add n-butyl isocyanate (99mg, 1mmol). Heat to reflux and add, by dropwise addition, oxalyl chloride (1.5mL). Purge with nitrogen at 130°–132° C. for 30 minutes and distill to give 2-chloro-4-isocyanatobenzenesulfonyl isocyanate.
Combine 4-isocyanato-2-chlorobenzenesulfonyl isocyanate (52mg, 0.2mmol), 5,7-dichloro-4-hydroxyquinoline-2-carboxylic acid, methyl ester (27.2mg, 0.1mmol) and acetonitrile (40mL). Relfux for 4 hours and add methanol (12mL) and reflux for several hours. Cool, filter and wash with acetonitrile. Triturate with boiling methanol (3mL) by stirring at reflux for 1 hour. Cool while continuing to stir and collect the solid by filtration to give title compound.

EXAMPLE 32

5,7-Dichloro-4-[4-amino-3-chlorobenzenesulfonimide]-1,4-dihydroquinoline-2-carboxylic acid

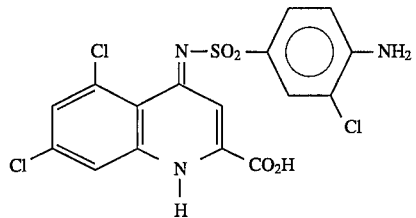

Combine 5,7-dichloro-4-[4-(methylcarbamoyl)-3-chlorobenzenesulfonimide]-1,4-dihydroquinoline-2-carboxylic acid, methyl ester (406mg, 0.78mmol), sodium hydroxide (0.94g, 2.3mmol), water (1.4mL), and methanol (6mL). Stir at reflux temperature under a nitrogen atmosphere for 36 hours. Remove solvent in vacuo and dilute with water (100mL). Adjust to pH 2 with 12N hydrochloric acid. Filter to give the title compound.

EXAMPLE 33

5,7-Dichloro-4-[4-amino-2-chlorobenzenesulfonimide]-1,4-dihydroquinoline-2-carboxylic acid

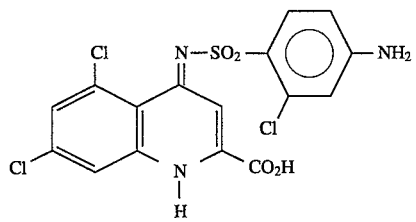

Combine 5,7-dichloro-4-[4-(methylcarbamoyl)-2-chlorobenzenesulfonimide]-1,4-dihydroquinoline-2-carboxylic acid, methyl ester (406mg, 0.78mmol), sodium hydroxide (0.94g, 2.3mmol), water (1.4mL), and methanol (6mL). Stir at reflux temperature under a nitrogen atmosphere for 36 hours. Remove solvent in vacuo and dilute with water (100mL).
Adjust to pH 2 with 12N hydrochloric acid. Filter to give the title compound.

EXAMPLE 34

5,7-Dichloro-4-[4-(acetylamino)benzenesulfonimide]-1,4-dihydroquinoline-2-carboxylic acid

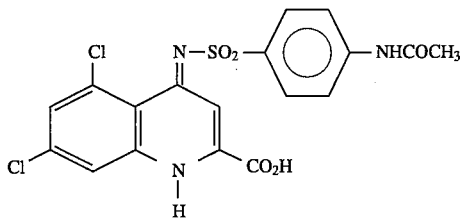

Mix 5,7-dichloro-4-[4-aminobenzenesulfonimide]-1,4-dihydroquinoline-2-carboxylic acid (4.13g, 10mmol) and pyridine (25mL). Cool to 10° C. and add, by dropwise addition, acetyl chloride (869mg, 11mmol). Allow to warm to room temperature and stir for 16 hours. Evaporate in vacuo, treat with water and filter to give the title compound.

EXAMPLE 35

5,7-Dichloro-4-[4-(benzoylamino)benzenesulfonimide]-1,4-dihydroquinoline-2-carboxylic acid

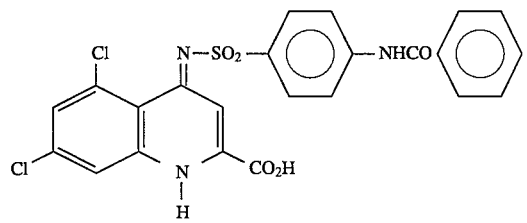

Mix 5,7-dichloro-4-[4-aminobenzenesulfonimide]-1,4-dihydroquinoline-2-carboxylic acid (0.82g, 2mmol) and pyridine (5mL). Cool to 10° C. and add, by dropwise addition, benzoyl chloride (0.58mL, 5mmol). Allow to warm to room temperature and stir for 16 hours. Evaporate in vacuo, treat with water and filter to give the title compound.

EXAMPLE 36

5-Bromo-7-fluoro-4-[4-(methylcarbamoyl)benzenesulfonimide]-1,4-dihydroquinoline-2-carboxylic acid, methyl ester

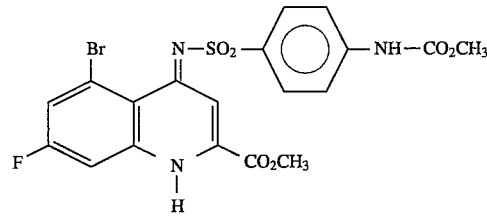

Combine 4-isocyanatobenzenesulfonyl isocyanate (1.01g, 4.5mmol), 5-bromo-7-fluoro-4-hydroxyquinoline-2-carboxylic acid, methyl ester (1.14g, 3.8mmol) and acetonitrile (8mL). Relfux for 16 hours, cool and filter to give 5-bromo-7-fluoro-4-[4-(isocyanato)benzenesulfonimide]-1,4-dihydroquinoline-2-carboxylic acid, methyl ester.
Treat 5-bromo-7-fluoro-4-[4-(isocyanato)benzenesulfonimide]-1,4-dihydroquinoline-2-carboxylic acid, methyl ester (2.24g, 4.5mmol) with methanol (125mL). Heat at reflux for 5 hours and evaporate the solvent in vacuo. Purify by chromatography to give the title compound.

EXAMPLE 37

5-Bromo-7-fluoro-4-[4-aminobenzenesulfonimide]-1,4-dihydroquinoline-2-carboxylic acid

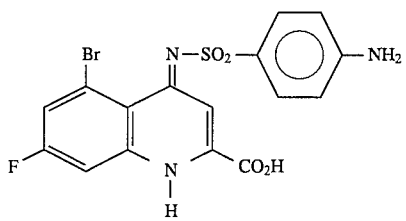

Combine 5-bromo-7-fluoro-4-[4-(methylcarbamoyl)benzenesulfonimide]-1,4-dihydroquinoline-2-carboxylic acid, methyl ester (401mg, 0.78mmol), sodium hydroxide (0.94g, 2.3mmol), water (1.4mL), and methanol (6mL). Stir at reflux temperature under a nitrogen atmosphere for 36 hours. Remove solvent in vacuo and dilute with water (100mL). Adjust to pH 2 with 12N hydrochloric acid. Filter to give the title compound.

The following compounds can be prepared analogously to that described in Example 25–37:
5,7-dibromo-4-[4-(methylcarbamoyl)benzenesulfonimide]-1,4-dihydroquinoline-2-carboxylic acid, methyl ester;
5-bromo-7-chloro-4-[4-(methylcarbamoyl)benzenesulfonimide]-1,4-dihydroquinoline-2-carboxylic acid, methyl ester;
5,7-dibromo-4-[4-aminobenzenesulfonimide]-1,4-dihydroquinoline-2-carboxylic acid;
5-bromo-7-chloro-4-[4-aminobenzenesulfonimide]-1,4-dihydroquinoline-2-carboxylic acid;
5,7-dibromo-4-[4-(acetylamido)benzenesulfonimide]-1,4-dihydroquinoline-2-carboxylic acid;
5-bromo-7-chloro-4-[4-(acetylamido)benzenesulfonimide]-1,4-dihydroquinoline-2-carboxylic acid;
5-bromo-7-chloro-4-[4-(trifluoromethylsulfonamido)-benzenesulfonimide]-1,4-dihydroquinoline-2-carboxylic acid;
5-bromo-7-chloro-4-[4-(benzenesulfonamido)benzenesulfonimide]-1,4-dihydroquinoline-2-carboxylic acid;
5-bromo-7-fluoro-4-[4-(acetylamido)benzenesulfonimide]-1,4-dihydroquinoline-2-carboxylic acid.
5,7-dichloro-4-[4-(trifluoromethylsulfonamide)-benzenesulfonimide]-1,4-dihydroquinoline-2-carboxylic acid.

The compounds of Formula I wherein X is represented by a phenyl derivative, A is represented by a substituent selected from the group consisting of hydrogen, OH, halogen, CN, $NO_2$, $C_1$–$C_6$ alkyl, $C_1$–$C_6$ alkoxy, $OCF_3$, $CF_{3'}$, B is a group represented $NH(CO)OR_3$ and D is represented by $C(O)OR_1$, wherein $R_1$ is hydrogen may be prepared using techniques and procedures well known and appreciated by one of ordinary skill in the art. A general synthetic procedure for preparing these compounds is set forth in Scheme C. In Scheme C, all substituents unless otherwise indicated are as previously defined.

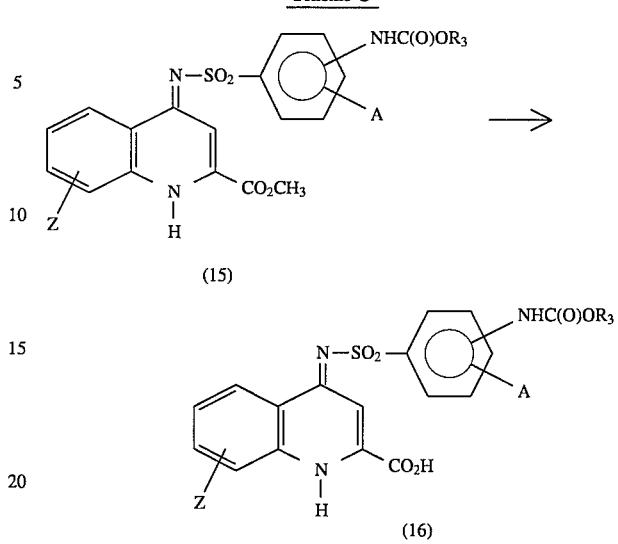

Scheme C

Scheme C provides a general synthetic procedure for preparing the compounds of Formula I wherein X is represented by a phenyl derivative, A is represented by a substituent selected from the group consisting of hydrogen, OH, halogen, CN, $NO_2$, $C_1$–$C_6$ alkyl, $C_1$–$C_6$ alkoxy, $OCF_3$, $CF_3$, B is a group represented $NH(CO)OR_3$ and D is represented by $C(O)OR_1$, wherein $R_1$ is hydrogen.

The methyl ester functionality of the appropriate 4-[(alkylcarbamoyl)benzenesulfonimide]-1,4-dihydroquinoline-2-carboxylic acid, methyl ester of structure (15) is hydrolyzed to give the corresponding 4-[(alkylcarbamoyl)benzenesulfonimide]-1,4-dihydroquinoline-2-carboxylic acid of structure (16).

For example, the appropriate 4-[(alkylcarbamoyl)benzenesulfonimide]-1,4-dihydroquinoline-2-carboxylic acid, methyl ester of structure (15) is contacted with a molar excess of an appropriate base such as lithium hydroxide. The reactants are typically contacted in a suitable solvent mixture such as methanol water. The reactants are typically stirred together at room temperature for a period of time ranging from 2–10 hours. The 4-[(alkylcarbamoyl)benzenesulfonimide]-1,4-dihydroquinoline-2-carboxylic acid of structure (16) is recovered from the reaction zone by extractive methods as is known in the art.

Starting materials for use in Scheme C are readily available to one of ordinary skill in the art.

The following example presents a typical synthesis as described in Scheme C. This example is understood to be illustrative only and is not intended to limit the scope of the present invention in any way.

EXAMPLE 38

5,7-Dichloro-4-[4-(methylcarbamoyl)benzenesulfonimide]-1,4-dihydroquinoline-2-carboxylic acid

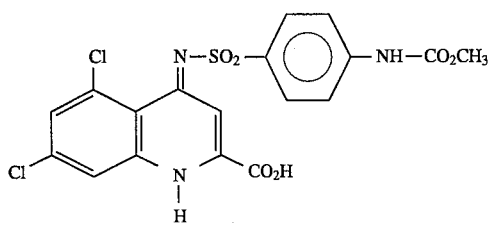

Combine 5,7-dichloro-4-[4-(methylcarbamoyl)benzenesulfonimide]-1,4-dihydroquinoline-2-carboxylic acid, methyl ester (242mg, 0.5mmol), lithium hydroxide hydrate (46mg, 1.5mmol), water (1mL) and methanol (3mL). Stir overnight at room temperature. Remove the methanol in vacuo and dilute with water (50mL). Adjust to pH 2 with 12N hydrochloric acid and filter. Crystallize from acetone/water to give the title compound (0.14g, 60%); mp 201°–202° C. (dec).
Anal. Calcd for $C_{18}H_{13}Cl_2N_3O_6S \cdot H_2O$: C, 44.27; H, 3.10; N, 8.61;
Found: C, 44.43; H, 3.16; N, 8.55.

EXAMPLE 39

5,7-Dichloro-4-[4-(ethylcarbamoyl)benzenesulfonimide]-1,4-dihydroquinoline-2-carboxylic acid

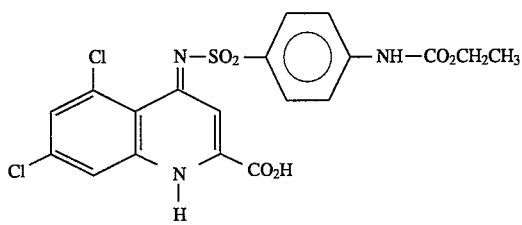

Combine 5,7-dichloro-4-[4-(ethylcarbamoyl)benzenesulfonimide]-1,4-dihydroquinoline-2-carboxylic acid, methyl ester (2.0g, 4.0mmol), lithium hydroxide hydrate (0.34g, 8mmol), water (25mL) and methanol (50mL). Stir overnight at room temperature. Remove the methanol in vacuo and dilute with water (100mL). Adjust to pH 2 with 12N hydrochloric acid and filter. Crystallize twice from acetone/water to give the title compound (1.35g, 70%); mp 162°–62° C. (dec).

Anal. Calcd for $C_{19}H_{15}Cl_2N_3O_6S \cdot H_2O$: C, 45.42; H, 3.41; N, 8.37;
Found: C, 45.38; H, 3.43; N, 8.45.

EXAMPLE 40

5,7-Dichloro-4-[4-(butylcarbamoyl)benzenesulfonimide]-1,4-dihydroquinoline-2-carboxylic acid

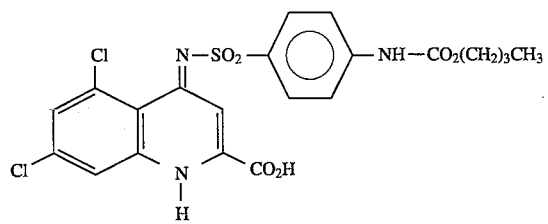

Combine 5,7-dichloro-4-[4-(butylcarbamoyl)benzenesulfonimide]-1,4-dihydroquinoline-2-carboxylic acid, methyl ester (2.0g, 3.8mmol), lithium hydroxide hydrate (0.319g, 7.5mmol), water (25mL) and methanol (50mL). Stir overnight at room temperature. Remove the methanol in vacuo and dilute with water (100mL). Adjust to pH 2 with 12N hydrochloric acid and filter. Crystallize from acetone/water to give the title compound (1.84g, 99%); mp 204°–205° C. (dec).
Anal. Calcd for $C_{21}H_{19}Cl_2N_3O_6S \cdot H_2O$: C, 47.56; H, 3.99; N, 7.92;
Found: C, 47.48; H, 3.97; N, 4.12.

The following compounds can be prepared analogously to those described in Examples 38–40:
5,7-Dibromo-4-[4-(methylcarbamoyl)benzenesulfonimide]-1,4-dihydroquinoline-2-carboxylic acid;
5-Bromo-7-fluoro-4-[4-(methylcarbamoyl)benzenesulfonimide]-1,4-dihydroquinoline-2-carboxylic acid;
5-Bromo-7-chloro-4-[4-(methylcarbamoyl)benzenesulfonimide]-1,4-dihydroquinoline-2-carboxylic acid.

The compounds of Formula I wherein X is represented by a phenyl derivative, A is represented by a substituent selected from the group consisting of hydrogen, OH, halogen, CN, $NO_2$, $C_1$–$C_6$ alkyl, $C_1$–$C_6$ alkoxy, $OCF_3$, $CF_3$, B is a group represented $NH_2$, $NHC(O)R_3$, $NHC(O)NHR_3$, $NHSO_2CF_3$, or $NHSO_2C_6H_5$ and D is represented by $C(O)OR_1$, wherein $R_1$ is $C_1$–$C_6$ alkyl or $C(O)NR_1R_2$ may be prepared using techniques and procedures well known and appreciated by one of ordinary skill in the art. A general synthetic procedure for preparing these compounds is set forth in Scheme D. In Scheme D, all substituents unless otherwise indicated are as previously defined.

Scheme D

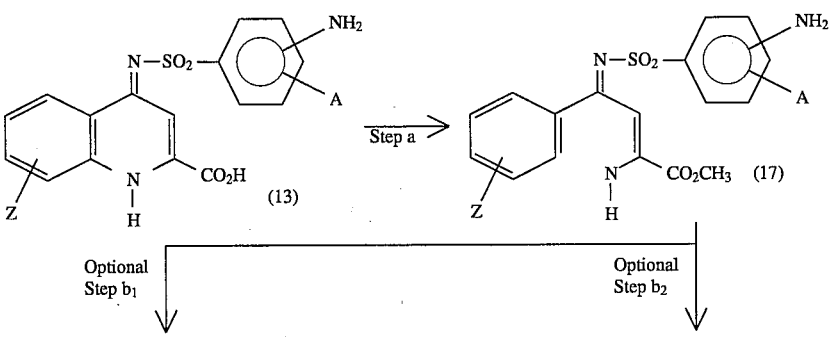

-continued
Scheme D

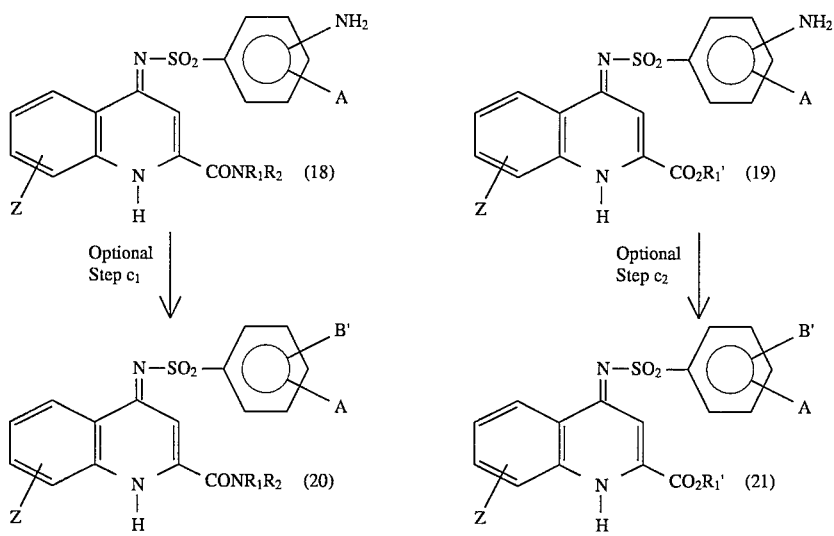

B' = NHC(O)R₃, NHC(O)NHR₃, NHSO₂CF₃ or NHSO₂C₆H₅
R₁' = C₁-C₆ alkyl

Scheme D provides a general synthetic scheme for preparing compounds of Formula I wherein X is represented by a phenyl derivative, A is represented by a substituent selected from the group consisting of hydrogen, OH, halogen, CN, $NO_2$, $C_1$-$C_6$ alkyl, $C_1$-$C_6$ alkoxy, $OCF_3$, $CF_3$, B is a group represented $NH_2$, $NHC(O)R_3$, $NHC(O)NHR_3$, $NHSO_2CF_3$, or $NHSO_2C_6H_5$ and D is represented by $C(O)OR_1$, wherein $R_1$ is $C_1$-$C_6$ alkyl, or $C(O)NR_1R_2$.

In step a, the carboxylic acid functionality of the appropriate 4-[(amino)benzenesulfonimide]-1,4-dihydroquinoline-2-carboxylic acid of structure (13) is esterfied to give the corresponding 4-[(amino)benzenesulfonimide]-1,4-dihydroquinoline-2-carboxylic acid, methyl ester of structure (17).

For example, the appropriate 4-[(amino)benzenesulfonimide]-1,4-dihydroquinoline-2-carboxylic acid of structure (13) is contacted with a molar excess of methanolic hydrochloric acid. The reactants are typically stirred together for a period of time ranging from 2–24 hours and at a temperature range of from room temperature to 60° C. The 4-[(amino)benzenesulfonimide]-1,4-dihydroquinoline-2-carboxylic acid, methyl ester of structure (17) is recovered from the reaction zone by extractive methods as is known in the art.

In optional step $b_1$, the methyl ester functionality of the appropriate 4-[(amino)benzenesulfonimide]-1,4-dihydroquinoline-2-carboxylic acid, methyl ester of structure (17) is amidated to give the corresponding 4-[(amino)benzenesulfonimide]-1,4-dihydroquinoline-2-carboxylic acid, carboxyamide of structure (18).

For example the appropriate 4-[(amino)benzenesulfonimide]-1,4-dihydroquinoline-2-carboxylic acid, methyl ester of structure (17) is contacted with a molar equivalent of an appropriate amine of the formula $NHR_1R_2$ and a catalytic amount of a amidation catalyst such as 2-hydroxypyridine or potassium cyanide. The reactants are typically stirred together for a period of time ranging from 2–24 hours and at a temperature range of from room temperature to reflux. The 4-[(amino)benzenesulfonimide]-1,4-dihydroquinoline-2-carboxyamide of structure (18) is recovered from the reaction zone by extractive methods as is known in the art.

In optional step $b_2$, the methyl ester functionality of the appropriate 4-[(amino)benzenesulfonimide]-1,4-dihydroquinoline-2-carboxylic acid, methyl ester of structure (17) is transesterified to give the corresponding 4-[(amino)benzenesulfonimide]-1,4-dihydroquinoline-2-carboxylic ester of structure (19).

For example the appropriate 4-[(amino)benzenesulfonimide]-1,4-dihydroquinoline-2-carboxylic acid, methyl ester of structure (17) is contacted with a molar excess of an appropriate alcohol of the formula $R_1OH$ and a catalytic amount of an acid such as concentrated sulfuric acid. The reactants are typically stirred together for a period of time ranging from 2–24 hours and at a temperature range of from room temperature to reflux. The 4-[(amino)benzenesulfonimide]-1,4-dihydroquinoline-2-carboxylic ester of structure (19) is recovered from the reaction zone by extractive methods as is known in the art.

In optional step $c_1$, the amine functionality of the appropriate 4-[(amino)benzenesulfonimide ]-1,4-dihydroquinoline-2-carboxyamide of structure (18) can be functionalized to give either the corresponding 4-[(amido)benzenesulfonimide]-1,4-dihydroquinoline-2-carboxyamide of structure (20), 4-[(ureido)benzenesulfonimide]-1,4-dihydroquinoline-2-carboxyamide of structure (20), 4-[(trifluoromethanesulfonamido)benzenesulfonimide]-1,4-dihydroquinoline-2-carboxyamide of structure (20) or 4-[(benzenesulfonamido)benzenesulfonimide]-1,4-dihydroquinoline-2-carboxyamide of structure (20) as described previously in Scheme B, optional step e.

In optional step $c_2$, the amine functionality of the appropriate 4-[(amino)benzenesulfonimide]-1,4-dihydroquinoline-2-carboxylic ester of structure (19) can be functionalized to give the corresponding 4-[(amido)benzenesulfonimide]-1,4-dihydroquinoline-2-carboxylic ester of structure (21), 4-[(ureido)benzenesulfonimide]-1,4-dihydroquinoline-2-carboxylic ester of structure (21), 4-[(trifluoromethanesulfonamido)-benzenesulfonimide]-1,4-dihydroquinoline-2-carboxylic ester of structure (21) or 4-[(benzenesulfonamido)benzenesulfonimide]-1,4-dihydroquinoline-2-carboxylic ester of structure (21) described previously in Scheme B, optional step e.

Starting materials for use in Scheme D are readily available to one of ordinary skill in the art.

The following examples present typical syntheses as described in Scheme D. These examples are understood to be illustrative only and are not intended to limit the scope of the present invention in any way.

EXAMPLE 41

5,7-Dichloro-4-[4-(amino)benzenesulfonimide]-1,4-dihydroquinoline-2-carboxylic acid, methyl ester

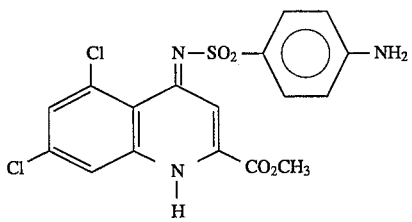

Dissolve 5,7-dichloro-4-[4-aminobenzenesulfonimide]-1,4-dihydroquinoline-2-carboxylic acid (413mg, 1mmol) in 0.5N methanolic hydrochloric acid (50mL). Stir at room temperature for 16 hours, cool and evaporate the solvent in vacuo. Add water to give a solid and filter to give the title compound; mp 219°–223° C.

Anal. Calcd for $C_{17}H_{13}Cl_2N_3O_4S$: C, 47.90; H, 3.07; N, 9.86;

Found: C, 47.94; H, 2.97; N, 9.59.

EXAMPLE 42

5,7-Dichloro-4-[4-(acetylamino)benzenesulfonimide]-1,4-dihydroquinoline-2-carboxylic acid, methyl ester

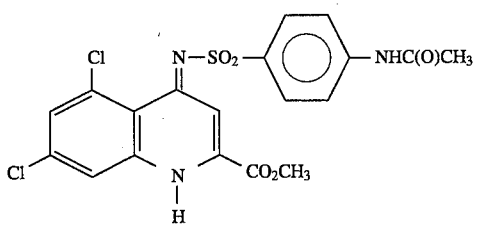

Combine 5,7-dichloro-4-[4-aminobenzenesulfonimide]-1,4-dihydroquinoline-2-carboxylic acid, methyl ester (4.27g, 10mmol) in pyridine (25mL). Cool to 10° C. and add, by dropwise addition, acetyl chloride (869mg, 11mmol). Allow to warm to room temperature and evaporate the pyridine in vacuo. Triturate with water and filter to give the title compound.

The following compounds can be prepared analogously to those described by Scheme D:

5,7-Dibromo-4-[4-(acetylamino)benzenesulfonimide]-1,4-dihydroquinoline-2-carboxylic acid, methyl ester;
5,7-dibromo-4-[4-aminobenzenesulfonimide]-1,4-dihydroquinoline-2-dimethylcarboxamide;
5-bromo-7-chloro-4-[4-aminobenzenesulfonimide]-1,4-dihydroquinoline-2-carboxylic acid, methyl ester;
5-bromo-7-fluoro-4-[4-aminobenzenesulfonimide]-1,4-dihydroquinoline-2-carboxylic acid, methyl ester;
5,7-dibromo-4-[4-(acetylamido)benzenesulfonimide]-1,4-dihydroquinoline-2-dimethylcarboxamide;
5-bromo-7-chloro-4-[4-(acetylamido)benzenesulfonimide]-1,4-dihydroquinoline-2-carboxylic acid, methyl ester;
5-bromo-7-chloro-4-[4-(trifluoromethylsulfonamido)-benzenesulfonimide]-1,4-dihydroquinoline-2-carboxylic acid, methyl ester;
5-bromo-7-chloro-4-[4-(benzenesulfonamido)benzenesulfonimide]-1,4-dihydroquinoline-2-carboxylic acid, methyl ester;
5-bromo-7-fluoro-4-[4-(acetylamido)benzenesulfonimide]-1,4-dihydroquinoline-2-carboxylic acid, methyl ester.
5,7-dichloro-4-[4-(trifluoromethylsulfonamide)phenylsulfonimide]-1,4-dihydroquinoline-2-carboxylic acid, methyl ester.

The compounds of Formula I wherein wherein X is represented by a phenyl derivative, A is represented by a substituent selected from the group consisting of hydrogen, OH, halogen, CN, $NO_2$, $C_1$–$C_6$ alkyl, $C_1$–$C_6$ alkoxy, $OCF_3$, $CF_3$, B is a group represented by $NR_1R_2$ and D is represented by $C(O)OR_1$ wherein $R_1$ is hydrogen may be prepared using techniques and procedures well known and appreciated by one of ordinary skill in the art. A general synthetic scheme for preparing these compounds is set forth in Scheme E. In Scheme E all substituents, unless otherwise indicated are as previously defined.

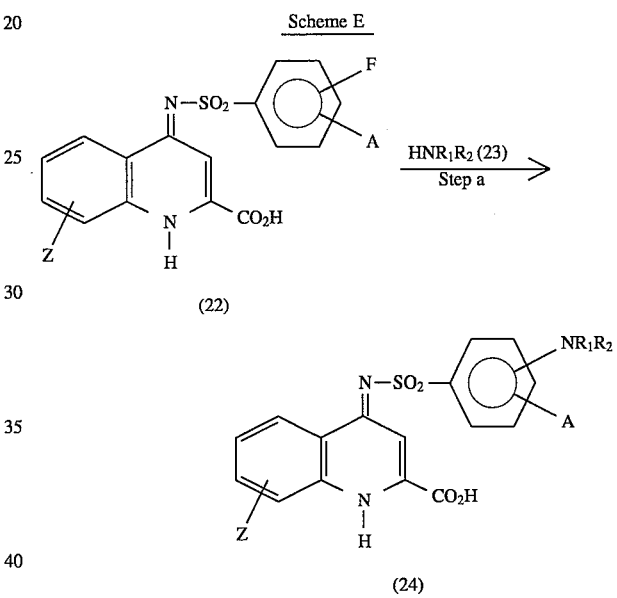

Scheme E provides a general synthetic scheme for preparing compounds of Formula I wherein wherein X is represented by a phenyl derivative, A is represented by a substituent selected from the group consisting of hydrogen, OH, halogen, CN, $NO_2$, $C_1$–$C_6$ alkyl, $C_1$–$C_6$ alkoxy, $OCF_3$, $CF_3$, B is a group represented by $NR_1R_2$ and D is represented by $C(O)OR_1$ wherein $R_1$ is hydrogen.

The aromatic fluoride of the appropriate 4-[fluorobenzenesulfonimide]-1,4-dihydroquinoline-2-carboxylic acid of structure (22) is displaced with an appropriate amine of structure (23) to give the 4-[dialkylaminobenzenesulfonimide]-1,4-dihydroquinoline-2-carboxylic acid of structure (24).

For example, the appropriate 4-[fluorobenzenesulfonimide]-1,4-dihydroquinoline-2-carboxylic acid of structure (22) is contacted with an excess amount of an appropriate amine of structure (23). The reactants are typically contacted in a suitable polar organic solvent, such as dimethyl sulfoxide. The reactants are typically stirred together for a period of time ranging from 4–10 hours and at a temperature range of from 50°–95° C. The 4-[dialkylaminobenzenesulfonimide]-1,4-dihydroquinoline-2-carboxylic acid of structure (24) is recovered from the reaction zone by extractive methods as is known in the art. It may be purified by silica gel chromatography.

Starting materials for use in Scheme E are readily available to one of ordinary skill in the art.

The following examples present typical syntheses as described in Scheme E. These examples are understood to be illustrative only and are not intended to limit the scope of the present invention in any way.

in the art. A general synthetic scheme for preparing these compounds is set forth in Scheme F. In Scheme F all substituents, unless otherwise indicated are as previously defined.

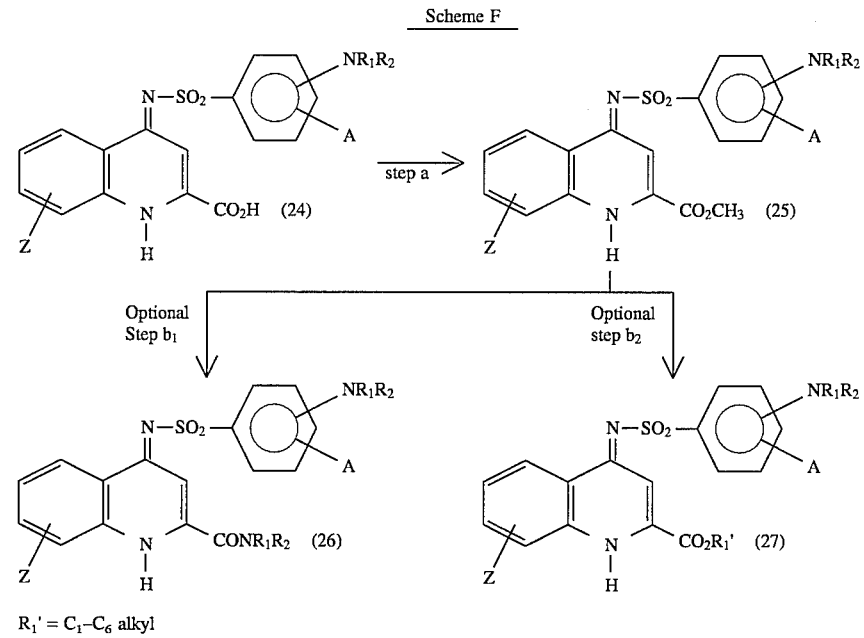

Scheme F

EXAMPLE 43

5,7-Dichloro-4-[4-(dimethylamino)benzenesulfonimide]1-1,4-dihydroguinoline-2-carboxylic acid

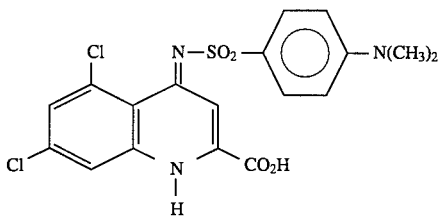

Pass dimethylamine gas through a solution of 5,7-dichloro-4-[4-fluorobenzenesulfonimide]-1,4-dihydroquinoline-2-carboxylic acid (12.5g, 0.03mol) in dimethyl sulfoxide (100mL) and keep at 80° C. for several hours and until absorption of the gas ceased. Pour the solution into water (600mL), acidify to pH 4 with hydrochloric acid and filter to give the title compound.

The following compounds can be prepared by analogy to those described in Example 43:
5,7-Dichloro-4-[4-(diethylamino)benzenesulfonimide]-1,4-dihydroquinoline-2-carboxylic acid;
5,7-Dichloro-4-[4-(t-butylamino)benzenesulfonimide]-1,4-dihydroquinoline-2-carboxylic acid.

The compounds of Formula I wherein wherein X is represented by a phenyl derivative, A is represented by a substituent selected from the group consisting of hydrogen, OH, halogen, CN, $NO_2$, $C_1$–$C_6$ alkyl, $C_1$–$C_6$ alkoxy, $OCF_3$, $CF_3$, B is a group represented by $NR_1R_2$ and D is represented by $C(O)OR_1$, wherein $R_1$ is $C_1$–$C_6$ alkyl, or $C(O)NR_1R_2$ may be prepared using techniques and procedures well known and appreciated by one of ordinary skill Scheme F provides a general synthetic scheme for preparing compounds of Formula I wherein wherein X is represented by a phenyl derivative, A is represented by a substituent selected from the group consisting of hydrogen, OH, halogen, CN, $NO_2$, $C_1$–$C_6$ alkyl, $C_1$–$C_6$ alkoxy, $OCF_3$, $CF_3$, B is a group represented by $NR_1R_2$ and D is represented by $C(O)OR_1$, wherein $R_1$ is $C_1$–$C_6$ alkyl, or $C(O)NR_1R_2$.

In step a, the carboxylic acid functionality of the appropriate 4-[(dialkylamino)benzenesulfonimide]-1,4-dihydroquinoline-2-carboxylic acid of structure (24) is esterfied to give the corresponding 4-[(dialkylamino)benzenesulfonimide]-1,4-dihydroquinoline-2-carboxylic acid, methyl ester of structure (25) as described previously in Scheme D, step a.

In optional step $b_1$, the methyl ester functionality of the appropriate 4-[(dialkylamino)benzenesulfonimide]-1,4-dihydroquinoline-2-carboxylic acid, methyl ester of structure (25) is amidated to give the corresponding 4-[(dialkylamino)benzenesulfonimide]-1,4-dihydroquinoline-2-carboxamide of structure (26) as described previously in Scheme E, optional step $b_1$.

In optional step $b_2$, the methyl ester functionality of the appropriate 4-[(dialkylamino)benzenesulfonimide]-1,4-dihydroquinoline-2-carboxylic acid, methyl ester of structure (25) is transesterified to give the corresponding 4-[(dialkylamino)benzenesulfonimide]-1,4-dihydroquinoline-2-carboxylic ester of structure (27) as described previously in Scheme D, optional step $b_2$.

Starting materials for use in Scheme F are readily available to one of ordinary skill in the art.

The following example presents a typical synthesis as described in Scheme F. This example is understood to be illustrative only and is not intended to limit the scope of the present invention in any way.

EXAMPLE 44

5,7-Dichloro-4-[4-(dimethylamino)benzenesulfonimide]-1,4-dihydroquinoline-2-carboxylic acid, methyl ester

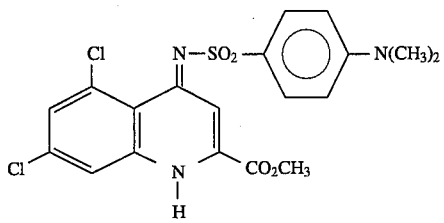

Dissolve 5,7-dichloro-4-[4-(dimethylamino)benzenesulfonimide]-1,4-dihydroquinoline-2-carboxylic acid (4.41g, 1mmol) in 1N methanolic hydrochloric acid (50mL). Heat at 60° C. for 16 hours, cool and evaporate the solvent in vacuo to give the title compound.

The following compounds can be prepared analogously to that described by Scheme F:

5,7-Dichloro-4-[4-(dimethylamino)benzenesulfonimide]-1,4-dihydroquinoline-2-carboxylic acid, ethyl ester;

5,7-Dichloro-4-[4-(dimethylamino)benzenesulfonimide]-1,4-dihydroquinoline-2-dimethylcarboxamide.

What is claimed is:

1. A compound of the formula:

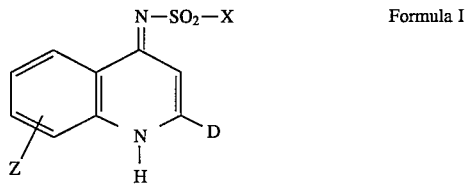

Formula I in which D is represented C(O)OR$_1$, C(O)NR$_1$R$_2$, wherein R$_1$ and R$_2$ are each independently represented by hydrogen or C$_1$–C$_6$ alkyl; Z is represented by a substituent selected from the group consisting of hydrogen, OH, halogen, CN, NO$_2$, C$_1$–C$_6$ alkyl, C$_1$–C$_6$ alkoxy, OCF$_3$ and CF$_3$; X is represented by one of the following substituents:

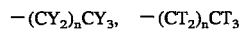

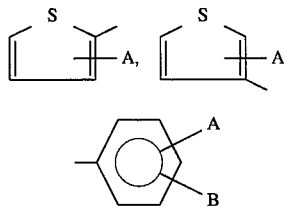

in which Y is represented by Cl; T is represented by F; n is represented by an integer from 0–3; A is represented by a substituent selected from the group consisting of hydrogen, OH, halogen, CN, NO$_2$, C$_1$–C$_6$ alkyl, C$_1$–C$_6$ alkoxy, OCF$_3$, CF$_3$; B is represented by one substituent selected from the group consisting of hydrogen, C(O)OR$_1$, C(O)NR$_1$R$_2$, NH$_2$, NR$_1$R$_2$, NHC(O)R$_3$, NHC(O)OR$_3$, NHC(O)NHR$_3$, NH—SO$_2$—CF$_3$, NH—SO$_2$—C$_6$H$_5$; in which R$_1$ and R$_2$ are as defined above and R$_3$ is C$_1$–C$_6$ alkyl; the pharmaceutically acceptable salts thereof and the tautomers thereof, with the proviso: 1) that when D is C(O)OCH$_3$ and X is phenyl in which A is para-methyl and B is hydrogen, then Z is not hydrogen, or a 5,7-dichloro substituent; 2) that when D is C(O)OC$_2$H$_5$ and X is phenyl in which A is para-methyl and B is hydrogen, then Z is not 6 methoxy, 7-methoxy or 5,8-dimethoxy and 3) that when B is not hydrogen, the total of A plus B may be up to 3 substituents.

2. A compound according to claim 1 in which D is represented by C(O)OR$_1$.

3. A compound according to claim 1 in which D is represented by C(O)NR$_1$R$_2$.

4. A compound according to claim 1 in which X is represented by —(CY$_2$)$_n$CY$_3$.

5. A compound according to claim 1 in which X is represented by —(CT$_2$)CT$_3$.

6. A compound according to claim 1 in which X is a phenyl derivative.

7. A compound according to claim 1 in which X is a 2-thiophene derivative.

8. A compound according to claim 1 in which X is a 3-thiophene derivative.

9. A compound according to claim 1 in which Z is a 5,7-halogen substituent.

10. A compound according to claim 1 in which said compound is 5,7-dichloro-4-[4-(trifluoromethyl)benzenesulfonimide]-1,4-dihydroquinoline-2-carboxylic acid, methyl ester.

11. A compound according to claim 1 in which said compound is 5,7-dichloro-4-[4-(trifluoromethyl)benzenesulfonimide]-1,4-dihydroquinoline-2-carboxylic acid.

12. A compound according to claim 1 in which said compound is 5,7-dichloro-4-[4-(fluoro)benzenesulfonimide]-1,4-dihydroquinilone-2-carboxylic acid, methyl ester.

13. A compound according to claim 1 in which said compound is 5,7-dichloro-4-[4-(fluoro)benzenesulfonimide]-1,4-dihydroquinilone-2-carboxylic acid.

14. A compound according to claim 1 in which said compound is 5,7-dichloro-4-[(2-thiophene)sulfonimide]-1,4-dihydroquinoline-2-carboxylic acid, methyl ester.

15. A compound according to claim 1 in which said compound is 5,7-dichloro-4-[(2-thiophene)sulfonimide]-1,4-dihydroquinoline-2-carboxylic acid.

16. A compound according to claim 1 in which said compound is 5,7-dichloro-4-[4-(methoxy)benzenesulfonimide]-1,4-dihydroquinoline-2-carboxylic acid.

17. A compound according to claim 1 in which said compound is 5,7-dichloro-4-[benzenesulfonimide]-1,4-dihydroquinoline-2-carboxylic acid, methyl ester.

18. A compound according to claim 1 in which said compound is 5,7-dichloro-4-[benzenesulfonimide]-1,4-dihydroquinoline-2-carboxylic acid.

19. A compound according to claim 1 in which said compound is 5,7-dichloro-4-[(4-methyl)benzenesulfonimide]-1,4-dihydroquinoline-2-carboxylic acid, methyl ester.

20. A compound according to claim 1 in which said compound is 5,7-dichloro-4-[(4-methyl)benzenesulfonimide]-1,4-dihydroquinoline-2-carboxylic acid.

21. A compound according to claim 1 in which said compound is 5,7-dichloro-4-[(4-chloro)benzenesulfonimide]-1,4-dihydroquinoline-2-carboxylic acid, methyl ester.

22. A compound according to claim 1 in which said compound is 5,7-dichloro-4-[(4-chloro)benzenesulfonimide]-1,4-dihydroquinoline-2-carboxylic acid.

23. A compound according to claim 1 in which said compound is 5,7-dichloro-4-[trifluoromethylsulfonimide]-1,4-dihydroquinolinebenzene-2-carboxylic acid, methyl ester.

24. A compound according to claim 1 in which said compound is 5,7-dichloro-4-[trifluoromethylsulfonimide]-1,4-dihydroquinoline-2-carboxylic acid.

25. A compound according to claim 1 in which said compound is 5-ethyl-7-bromo-4-[benzenesulfonimide]-1,4-dihydroquinoline-2-carboxylic acid, ethyl ester.

26. A compound according to claim 1 in which said compound is 5-ethyl-7-bromo-4-[benzenesulfonimide]-1,4-dihydroquinoline-2-carboxylic acid.

27. A compound according to claim 1 in which said compound is 5-bromo-7-fluoro-4-[benzenesulfonimide]-1,4-dihydroquinoline-2-carboxylic acid, methyl ester.

28. A compound according to claim 1 in which said compound is 5-bromo-7-fluoro-4-[benzenesulfonimide]-1,4-dihydroquinoline-2-carboxylic acid.

29. A compound according to claim 1 in which said compound is 5,7-dichloro-4-[2-chlorobenzenesulfonimide]-1,4-dihydroquinoline-2-carboxylic acid, methyl ester.

30. A compound according to claim 1 in which said compound is 5,7-dichloro-4-[2-chlorobenzenesulfonimide]-1,4-dihydroquinoline-2-carboxylic acid.

31. A compound according to claim 1 in which said compound is 5,7-dichloro-4-[3-chlorobenzenesulfonimide]-1,4-dihydroquinoline-2-carboxylic acid, methyl ester.

32. A compound according to claim 1 in which said compound is 5,7-dichloro-4-[3-chlorobenzenesulfonimide]-1,4-dihydroquinoline-2-carboxylic acid.

33. A compound according claim 1 in which said compound is 5,7-dichloro-4-[4-(hydroxy)benzenesulfonimide]-1,4-dihydroquinoline-2-carboxylic acid.

34. A compound according to claim 1 in which said compound is 5,7-dibromo-4-[benzenesulfonimide]-1,4-dihydroquinoline-2-carboxylic acid.

35. A compound according to claim 1 in which said compound is 5-bromo-7-chloro-4-[benzenesulfonimide]-1,4-dihydroquinoline-2-carboxylic acid.

36. A compound according to claim 1 in which said compound is 5,7-dichloro-4-[4-(methylcarbamoyl)benzenesulfonimide]-1,4-dihydroquinoline-2-carboxylic acid, methyl ester.

37. A compound according to claim 1 in which said compound is 5,7-dichloro-4-[4-(ethylcarbamoyl)benzenesulfonimide]-1,4-dihydroquinoline-2-carboxylic acid, methyl ester.

38. A compound according to claim 1 in which said compound is 5,7-dichloro-4-[4-(butylcarbamoyl)benzenesulfonimide]-1,4-dihydroquinoline-2-carboxylic acid, methyl ester.

39. A compound according to claim 1 in which said compound is 5,7-dichloro-4-[4-(methylureido)benzenesulfonimide]-1,4-dihydroquinoline-2-carboxylic acid, methyl ester.

40. A compound according to claim 1 in which said compound is 5,7-dichloro-4-[4-aminobenzenesulfonimide]-1,4-dihydroquinoline-2-carboxylic acid.

41. A compound according to claim 1 in which said compound is 5,7-dichloro-4-[4-(methylcarbamoyl)-3-chlorobenzenesulfonimide]-1,4-dihydroquinoline-2-carboxylic acid, methyl ester.

42. A compound according to claim 1 in which said compound is 5,7-dichloro-4-[4-(methylcarbamoyl)-2-chlorobenzenesulfonimide]-1,4-dihydroquinoline-2-carboxylic acid, methyl ester.

43. A compound according to claim 1 in which said compound is 5,7-dichloro-4-[4-amino-3-chlorobenzenesulfonimide]-1,4-dihydroquinoline-2-carboxylic acid.

44. A compound according to claim 1 in which said compound is 5,7-dichloro-4-[4-amino-2-chlorobenzenesulfonimide]-1,4-dihydroquinoline-2-carboxylic acid.

45. A compound according to claim 1 in which said compound is 5,7-dichloro-4-[4-(acetylamino)benzenesulfonimide]-1,4-dihydroquinoline-2-carboxylic acid.

46. A compound according to claim 1 in which said compound is 5,7-dichloro-4-[4-(benzoylamino)benzenesulfonimide]-1,4-dihydroquinoline-2-carboxylic acid.

47. A compound according to claim 1 in which said compound is 5-bromo-7-fluoro-4-[4-(methylcarbamoyl)benzenesulfonimide]-1,4-dihydroquinoline-2-carboxylic acid, methyl ester.

48. A compound according to claim 1 in which said compound is 5-bromo-7-fluoro-4-[4-aminobenzenesulfonimide]-1,4-dihydroquinoline-2-carboxylic acid.

49. A compound according to claim 1 in which said compound is 5,7-dibromo-4-[4-(methylcarbamoyl)benzenesulfonimide]-1,4-dihydroquinoline-2-carboxylic acid, methyl ester.

50. A compound according to claim 1 in which said compound is 5-bromo-7-chloro-4-[4-(methylcarbamoyl)benzenesulfonimide]-1,4-dihydroquinoline-2-carboxylic acid, methyl ester.

51. A compound according to claim 1 in which said compound is 5,7-dibromo-4-[4-aminobenzenesulfonimide]-1,4-dihydroquinoline-2-carboxylic acid.

52. A compound according to claim 1 in which said compound is 5-bromo-7-chloro-4-[4-aminobenzenesulfonimide]-1,4-dihydroquinoline-2-carboxylic acid.

53. A compound according to claim 1 in which said compound is 5,7-dibromo-4-[4-(acetylamido)benzenesulfonimide]-1,4-dihydroquinoline-2-carboxylic acid.

54. A compound according to claim 1 in which said compound is 5-bromo-7-chloro-4-[4-(acetylamido)benzenesulfonimide]-1,4-dihydroquinoline-2-carboxylic acid.

55. A compound according to claim 1 in which said compound is 5-bromo-7-chloro-4-[4-(trifluoromethylsulfonamido)benzenesulfonimide]-1,4-dihydroquinoline-2-carboxylic acid.

56. A compound according to claim 1 in which said compound is 5-bromo-7-chloro-4-[4-(benzenesulfonamido)-benzenesulfonimide]-1,4-dihydroquinoline-2-carboxylic acid.

57. A compound according to claim 1 in which said compound is 5-bromo-7-fluoro-4-[4-(acetylamido)benzenesulfonimide]-1,4-dihydroquinoline-2-carboxylic acid.

58. A compound according to claim 1 in which said compound is 5,7-dichloro-4-[4-(trifluoromethylsulfonamide)-benzenesulfonimide]-1,4-dihydroquinoline-2-carboxylic acid.

59. A compound according to claim 1 in which said compound is 5,7-dichloro-4-[4-(methylcarbamoyl)benzenesulfonimide]-1,4-dihydroquinoline-2-carboxylic acid.

60. A compound according to claim 1 in which said compound is 5,7-dichloro-4-[4-(ethylcarbamoyl)benzenesulfonimide]-1,4-dihydroquinoline-2-carboxylic acid.

61. A compound according to claim 1 in which said compound is 5,7-dichloro-4-[4-(butylcarbamoyl)benzenesulfonimide]-1,4-dihydroquinoline-2-carboxylic acid.

62. A compound according to claim 1 in which said compound is 5,7-dibromo-4-[4-(methylcarbamoyl)benzenesulfonimide]-1,4-dihydroquinoline-2-carboxylic acid.

63. A compound according to claim 1 in which said compound is 5-bromo-7-chloro-4-[4-(methylcarbamoyl)benzenesulfonimide]-1,4-dihydroquinoline-2-carboxylic acid.

64. A compound according to claim 1 in which said compound is 5-bromo-7-chloro-4-[4-(methylcarbamoyl)benzenesulfonimide]-1,4-dihydroquinoline-2-carboxylic acid.

65. A compound according to claim 1 in which said compound is 5,7-dichloro-4-[4-(amino)benzenesulfonimide]-1,4-dihydroquinoline-2-carboxylic acid, methyl ester.

66. A compound according to claim 1 in which said compound is 5,7-dichloro-4-[4-(acetylamino)benzenesulfonimide]-1,4-dihydroquinoline-2-carboxylic acid, methyl ester.

67. A compound according to claim 1 in which said compound is 5,7-dibromo-4-[4-(acetylamino)benzenesulfonimide]-1,4-dihydroquinoline-2-carboxylic acid, methyl ester.

68. A compound according to claim 1 in which said compound is 5,7-dibromo-4-[4-(aminobenzenesulfonimide]-1,4-dihydroquinoline-2-dimethylcarboxamide.

69. A compound according to claim 1 in which said compound is 5-bromo-7-chloro-4-[4-aminobenzenesulfonimide]-1,4-dihydroquinoline-2-carboxylic acid, methyl ester.

70. A compound according to claim 1 in which said compound is 5-bromo-7-fluoro-4-[4-aminobenzenesulfonimide]-1,4-dihydroquinoline-2-carboxylic acid, methyl ester.

71. A compound according to claim 1 in which said compound is 5,7-dibromo-4-[4-(acetylamido)benzenesulfonimide]-1,4-dihydroquinoline-2-dimethylcarboxamide.

72. A compound according to claim 1 in which said compound is 5-bromo-7-chloro-4-[4-(acetylamido)benzenesulfonimide]-1,4-dihydroquinoline-2-carboxylic acid, methyl ester.

73. A compound according to claim 1 in which said compound is 5-bromo-7-chloro-4-[4-(trifluoromethylsulfonimide]-1,4-dihydroquinoline-2-carboxylic acid, methyl ester.

74. A compound according to claim 1 in which said compound is 5-bromo-7-chloro-4-[4-(benzenesulfonamido)-benzenesulfonimide]-1,4-dihydroquinoline-2-carboxylic acid, methyl ester.

75. A compound according to claim 1 in which said compound is 5-bromo-7-fluoro-4-[4-(acetylamido)benzenesulfonimide]-1,4-dihydroquinoline-2-carboxylic acid, methyl ester.

76. A compound according to claim 1 in which said compound is 5,7-dichloro-4-[4-(trifluoromethylsulfonimide)phenylsulfonimide]-1,4-dihydroquinoline-2-carboxylic acid, methyl ester.

77. A compound according to claim 1 in which said compound is 5,7-dichloro-4-[4-(dimethylamino)benzenesulfonimide]-1,4-dihydroquinoline-2-carboxylic acid.

78. A compound according to claim 1 in which said compound is 5,7-dichloro-4-[4-(dimethylamino)benzenesulfonimide]-1,4-dihydroquinoline-2-carboxylic acid.

79. A compound according to claim 1 in which said compound is 5,7-dichloro-4-[4-(t-butylamino)benzenesulfonimide]-1,4-dihydroquinoline-2-carboxylic acid.

80. A compound according to claim 1 in which said compound is 5,7-dichloro-4-[4-(dimethylamino)benzenesulfonimide]-1,4-dihydroquinoline-2-carboxylic acid, methyl ester.

81. A compound according to claim 1 in which said compound is 5,7-dichloro-4-[4-(dimethylamino)benzenesulfonimide]-1,4-dihydroquinoline-2-carboxylic acid, ethyl ester.

82. A compound according to claim 1 in which said compound is 5,7-dichloro-4-[4-(dimethylamino)benzenesulfonimide]-1,4-dihydroquinoline-2-dimethylcarboxamide.

\* \* \* \* \*